US007381561B2

(12) United States Patent
Uchida et al.

(10) Patent No.: US 7,381,561 B2
(45) Date of Patent: Jun. 3, 2008

(54) ENRICHED CENTRAL NERVOUS SYSTEM STEM CELL AND PROGENITOR CELL POPULATIONS, AND METHODS FOR IDENTIFYING, ISOLATING AND ENRICHING FOR SUCH POPULATIONS

(75) Inventors: Nobuko Uchida, Palo Alto, CA (US); Alexandra Capela, Mountain View, CA (US)

(73) Assignee: StemCells California, Inc., Palo Alto, CA (US)

( * ) Notice: Subject to any disclaimer, the term of this patent is extended or adjusted under 35 U.S.C. 154(b) by 301 days.

(21) Appl. No.: 10/649,234

(22) Filed: Aug. 27, 2003

(65) Prior Publication Data

US 2004/0137535 A1 Jul. 15, 2004

Related U.S. Application Data

(60) Provisional application No. 60/406,546, filed on Aug. 27, 2002.

(51) Int. Cl.
*C12N 5/08* (2006.01)
(52) U.S. Cl. .................................... 435/368; 435/332
(58) Field of Classification Search ............... 435/332, 435/368; 424/140.1
See application file for complete search history.

(56) References Cited

U.S. PATENT DOCUMENTS

| 4,683,195 | A | 7/1987 | Mullis et al. | 435/6 |
|---|---|---|---|---|
| 4,683,202 | A | 7/1987 | Mullis | 435/91 |
| 5,750,376 | A | 5/1998 | Weiss et al. | 435/69.52 |
| 5,753,506 | A | 5/1998 | Johe | 435/377 |
| 5,843,633 | A | 12/1998 | Yin et al. | 435/2 |
| 5,851,832 | A | 12/1998 | Weiss et al. | 435/368 |
| 6,468,794 | B1 | 10/2002 | Uchida et al. | 435/368 |
| 2001/0051372 | A1 | 12/2001 | Yin et al. | 435/325 |
| 2003/0040023 | A1 | 2/2003 | Klassen et al. | 435/7.21 |
| 2003/0109039 | A1 | 6/2003 | Buck et al. | 435/368 |

FOREIGN PATENT DOCUMENTS

| EP | 0 438 520 B1 | 7/1991 |
|---|---|---|
| WO | WO 90/07380 | 7/1990 |
| WO | WO 95/13103 | 5/1995 |
| WO | WO 96/26782 | 9/1996 |
| WO | WO 00/47762 | 8/2000 |

OTHER PUBLICATIONS

Klassen et al. *Neurosci. Lett.*, 312:180-182 (2001).
Allendoerfer et al., "Forse-1, an antibody that labels regionally restricted subpopulations of progenitor cells in the embryonic central nervous system, recognizes the Le$^x$ carbohydrate on a proteoglycan and two glycolipid antigens", *Mol. Cell. Neurosci.*, 6:381-395 (1995).
Allendoerfer et al., "Morphological domains of Lewis-X/FORSE-1 immunolabeling in the embryonic neural tube are due to developmental regulation of cell surface carbohydrate expression", *Dev. Biol.*, 211:208-219 (1999).
Ashwell et al., "Developmental expression of the CD15 epitope in the hippocampus of the mouse", *Cell Tissue Res.*, 289(1):17-23 (1997).
Bach et al., "Stem cells: the intestinal stem cell as a paradigm", *Carcinogenesis*, 21(3):469-476 (2000).
Bartsch et al., "Distribution of the 3-fucosyl-N-acetyl-lactosamine (FAL) epitope in the adult mouse brain", *Cell Tissue Res.*, 263:353-366 (1991).
Bird et al., "Oligosaccharides containing fucose linked $\alpha$(1-3) and $\alpha$(1-4) to N-acetyglucosamine cause decompaction of mouse morulae", *Dev. Biol.*, 104(2):449-460 (1984).
Calaora et al., "mCD24 expression in the developing mouse brain and in zones of secondary neurogenesis in the adult", *Neuroscience*, 73(2):581-594 (1996).
Campos-Ortega, J.A., "Genetic mechanisms of early neurogenesis in drosophila melanogaster", *Mol. Neurobiol.*, 10:75-89 (1995).
Cao et al., "Pluripotent stem cells engrafted into the normal or lesioned adult rat spinal cord are restricted to a glial lineage", *Exp. Neurol.*, 167(1):48-58 (2001).
Chiasson et al., "Adult mammalian forebrain ependymal and subependymal cells demonstrate proliferative potential, but only subependymal cells have neural stem cell characteristics", *J. Neurosci.*, 19(11):462-4471 (1999).
Davis et al., "A self-renewing multipotential stem cell in embryonic rat cerebral cortex", *Nature*, 372:263-266 (1994).
Dodd et al., "Cell surface glycoconjugates and carbohydrate-binding proteins: possible recognition signals in sensory neurone development", *J. Exp. Biol.*, 124:225-238 (1986).
Doetsch et al., "Subventricular zone astrocytes are neural stem cells in the adult mammalian brain", *Cell*, 97(6):703-716(1999).
Doetsch et al., "Regeneration of a germinal layer in the adult mammalian brain", *Proc. Natl. Acad. Sci. USA*, 96(20):11619-11624 (1999).
Dvořák et al., "Embryoglycan ectodomains regulate biological activity of FGF-2 to embryonic stem cells", *J. Cell Sci.*, 111(19):2945-2952 (1998).
Fox et al., "Immunohistochemical localization of the early embryonic antigen (SSEA-1) in postimplantation mouse embyos and fetal and adult tissues", *Dev. Biol.*, 83(2):391-398 (1981).
Gage, F.H., "Mammalian neural stem cells", *Science*, 287:1433-1438 (2000).
Gocht et al., "CD15-containing glycoconjugates in the central nervous system", *Histol. Histopathol.*, 11:1007-1028 (1996).

(Continued)

*Primary Examiner*—Robert C. Hayes
(74) *Attorney, Agent, or Firm*—Mintz, Levin, Cohn, Ferris, Glovsky and Popeo, PC; Ivor R. Elrifi; Christina K. Stock

(57) ABSTRACT

Enriched neural stem and progenitor cell populations, and methods for identifying, isolating and enriching for neural stem cells using reagents that bind to cell surface markers are provided.

26 Claims, 8 Drawing Sheets

OTHER PUBLICATIONS

Gomperts et al., "Interactions between primordial germ cells play a role in their migration in mouse embryos", *Development*, 120:135-141 (1994).

Gooi et al., "Stage-specific embryonic antigen involves α1-3 fucosylated type 2 blood group chains", *Nature*, 292:156-158 (1981).

Gould et al., "Neurogenesis in the neucortex of adult primates", *Science*, 286:548-552 (1999).

Gritti et al., "Multipotential stem cells from the adult mouse brain proliferate and self-renew in response to basic fibroblast growth factor", *J. Neurosci.*, 16(3):1091-1100 (1996).

Gritti et al., "Multipotent neural stem cells reside into the rostral extension and olfactory bulb of adult rodents", *J. Neurosci.*, 22(2):437-445 (2002).

Hakomori, S., "Le$^x$ and related structures as adhesion molecules", *Histochem. J.*, 24(11):771-776 (1992).

Jessell et al., "Carbohydrates and carbohydrate-binding proteins in the nervous system", *Annu. Rev. Neurosci.*, 13:227-255 (1990).

Jirmanova et al., "O-linked carbohydrates are required for FGF-2-mediated proliferation of mouse embryonic cells", *Int. J. Dev. Biol.*, 43(6):555-562 (1999).

Johansson et al., "Identification of a neural stem cell in the adult mammalian central nervous system", *Cell*, 96(1):25-34 (1999).

Jones et al., "Stem cell patterning and fate in human epidermis", *Cell*,80(1):83-93 (1995).

Kato et al., "Physiological degradation converts the soluble syndecan-1 ectodomain from an inhibitor to a potent activator of FGF-2", *Nat. Med.*, 4(6):691-697 (1998).

Kawaguchi et al., "Nestin-EGFP transgenic mice: visualization of the self-renewal and multipotency of CNS stem cells", *Mol. Cell. Neurosci.*, 17(2):259-273 (2001).

Kempermann et al., "Genetic influence on neurogenesis in the dentate gyrus of adult mice", *Proc. Natl. Acad. Sci. USA*, 94(19):10409-10414 (1997).

Kondo et al., "Oligodendrocyte precursor cells reprogrammed to become multipotential CNS stem cells", *Science*, 289:1754-1757 (2000).

Laywell et al., "Identification of a multipotent astrocytic stem cell in the immature and adult mouse brain", *Proc. Natl. Acad. Sci. USA*, 97(25):13883-13888 (2000).

Lois et al., "Proliferating subventricular zone cells in the adult mammalian forebrain can differentiate into neurons and glia", *Proc. Natl. Acad. Sci. USA*, 90:2074-2077 (1993).

Mai et al., "Demarcation of prosencephalic regions by CD15-positive radial glia", *Eur. J. Neurosci.*, 10(2):746-751 (1998).

Marani et al., "A longitudinal band-pattern for the monoclonal human granulocyte antibody $B_{4,3}$ in the cerebellar external granular layer of the immature rabbit", *Histochem.*, 78(2):157-161 (1983).

Marani et al., "Stage specific embryonic carbohydrate surface antigens of primordial germ cells in mouse embryos: FAL (S.S.E.A.-1) and globoside (S.S.E.A.-3)", *Acta Morphol. Neerl.-Scand.*, 24(2):103-110 (1986).

Marmur et al., "Isolation and developmental characterization of cerebral cortical multipotent progenitors", *Dev. Biol.*, 204:577-591 (1998).

Milev et al., "The core protein of the chondroitin sulfate proteoglycan phosphacan is a high-affinity ligand of fibroblast growth factor-2 and potentiates its mitogenic activity", *J. Biol. Chem.*, 273(34):21439-21442 (1998).

Morrison et al., "Regulatory mechanisms in stem cell biology", *Cell*, 88(3):287-298 (1997).

Morrison et al., "Prospective identification, isolation by flow cytometry, and in vivo self-renewal of multipotent mammalian neural crest stem cells", *Cell*, 96(5):737-749 (1999).

Morshead et al., "Neural stem cells in the adult mammalian forebrain: a relatively quiescent subpopulation of subependymal cells", *Neuron*, 13(5):1071-1082 (1994).

Muramatsu, T., "Cell surface glycoproteins: biochemical, immunological and molecular biological studies", *Nagoya J. Med. Sci.*, 57:95-108 (1994).

Nowakowski et al., "New neurons: extraordinary evidence or extraordinary conclusion?", *Science*, 288:771a-773a (2000).

Palmer et al., "The adult rat hippocampus contains primordial neural stem cells", *Mol. Cell. Neurosci.*, 8(6):389-404 (1997).

Palmer et al., "Vascular niche for adult hippocampal neurogenesis", *J. Comp. Neurol.*, 425(4):479-494 (2000).

Reynolds et al., "Oligodendroglial progenitors labeled with the O4 antibody persist in the adult rat cerebral cortex in vivo", *J. Neurosci. Res.*, 47(5):455-470 (1997).

Raynolds et al., "Generation of neurons and astrocytes from isolated cells of the adult mammalian central nervous system", *Science*, 255:1707-1710 (1992).

Rietze et al., "Purification of a pluripotent neural stem cell from the adult mouse brain", *Nature*, 412:736-739 (2001).

Sakakibara et al., "Mouse-musashi-1, a neural RNA-binding protein highly enriched in the mammalian CNS stem cell", *Dev. Biol.*, 176:230-242 (1996).

Seaberg et al., "Adult rodent neurogenic regions: the ventricular subependyma contains neural stem cells, but the dentate gyrus contains restricted progenitors", *J. Neurosci.*, 22(5):1784-1793 (2002).

Solter et al., "Monoclonal antibody defining a stage-specific mouse embryonic antigen (SSEA-1)", *Proc. Natl. Acad. Sci. USA*, 75(11):5565-5569 (1978).

Suhonen et al., "Differentiation of adult hippocampus-derived progenitors into olfactory neurons in vivo", *Nature*, 383:624-627 (1996).

Tole et al., "FORSE-1: a positionally regulated epitope in the developing rat central nervous system", *J. Neurosci.*, 15(2):957-969 (1995).

Uchida et al., "Direct isolation of human central nervous system stem cells", *Proc. Natl. Acad. Sci. USA*, 97(26):14720-14725 (2000).

Weiss et al., "Multipotent CNS stem cells are present in the adult mammalian spinal cord and ventricular neuroaxis", *J. Neurosci.*, 16(23):7599-7609 (1996).

Winkler et al., "Incorporation and glial differentiation of mouse EGF-responsive neural progenitor cells after transplantation into the embryonic rat brain", *Mol. Cell. Neurosci.*, 11(3):99-116 (1998).

Yamamoto et al., "Fucose-containing glycolipids are stage- and region-specific antigens in developing embryonic brain of rodents", *Proc. Natl. Acad. Sci. USA*, 82:3045-3049 (1985).

Accession No. NM_002033, Mar. 24, 1999.

Akashi et al., "A Clonogenic Common Myeloid Progenitor that Gives Rise to All Myeloid Lineages", *Nature*, 404:193-197 (2000).

Corbeil et al., "AC133 Hematopoietic Stem Cell Antigen: Human Homologue of Mouse Kidney Prominin or Distinct Member of a Novel Protein Family?", *Blood*, 91(7):2625-2626 (1998).

Corbeil et al., "Selective Localization of the Polytopic Membrane Protein Prominin in Microvilli of Epithelial Cells - A Combination of Apical Sorting and Retention in Plasma Membrane Protrusions", *J. Cell Sci.*, 112(Pt. 7):1023-1033 (1999).

Jost et al., "Mammalian Expression and Secretion of Functional Single-chain Fv Molecules", *J. Biol. Chem.*, 269(42):26267-26273 (1994).

Kabat et al., "Sequences of Proteins of Immunological Interest ", vol. I, Fifth Edition, U.S. Department of Health and Human Services, pp. 1-44 (1991).

Lendahl et al., "CNS Stem Cells Express a New Class of Intermediate Filament Protein", *Cell*, 60:585-595 (1990).

Liu et al., "Chimeric Mouse-Human IgG1 Antibody that Can Mediate Lysis of Cancer Cells", *Proc. Natl. Acad. Sci. USA*, 84:3439-3443 (1987).

Liu et al., "Production of a Mouse-Human Chimeric Monoclonal Antibody to CD20 With Potent Fo- Dependent Biologic Activity", *J. Immunol.*, 139(10):3521-3526 (1987).

Miraglia et al., "A Response to AC133 Hematopietic Stem Cell Antigen: Human Homologue of Mouse Kidney Prominin or Distinct Member of a Novel Protein Family?", *Blood*, 91(11):4390-4391 (1988).

Simmons et al., "Molecular Cloning of a cDNA Encoding CD34, a Sialomucin fo Human Hematopietic Stem Cells", *J. Immunol.*, 148(1):267-271 (1992).

Tamura et al., "Epithelial Integrin $\alpha_6\beta_4$: Complete Primary Structure of $\alpha_6$ and Variant Forms of $\beta_4$", *J. Cell Biol.*, 111:1593-1604 (1990).

Weigmann et al., "Prominin, A Novel Microvilli-Specific Polytopic Membrane Protein of the Apical Surface of Epithelial Cells, Is Targeted to Plasmalemmal Protrusions of Non-Epithelial Cells", *Proc. Natl. Acad. Sci. USA*, 94(23):12425-12430 (1997).

Figure 3 (Example 1)
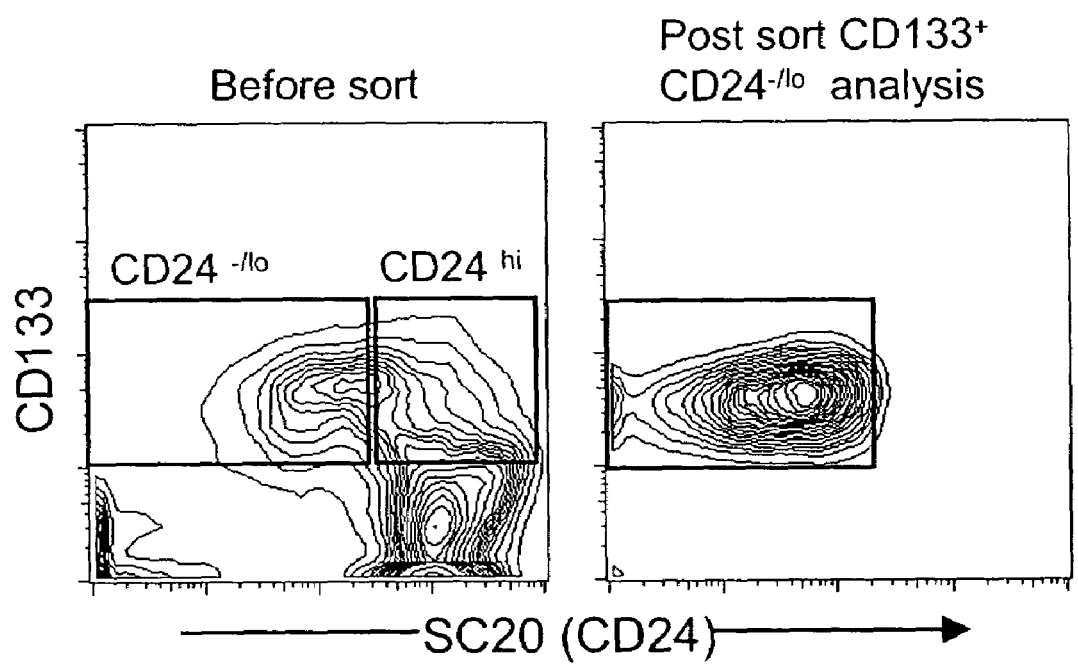

Figure 4 (Example 2)
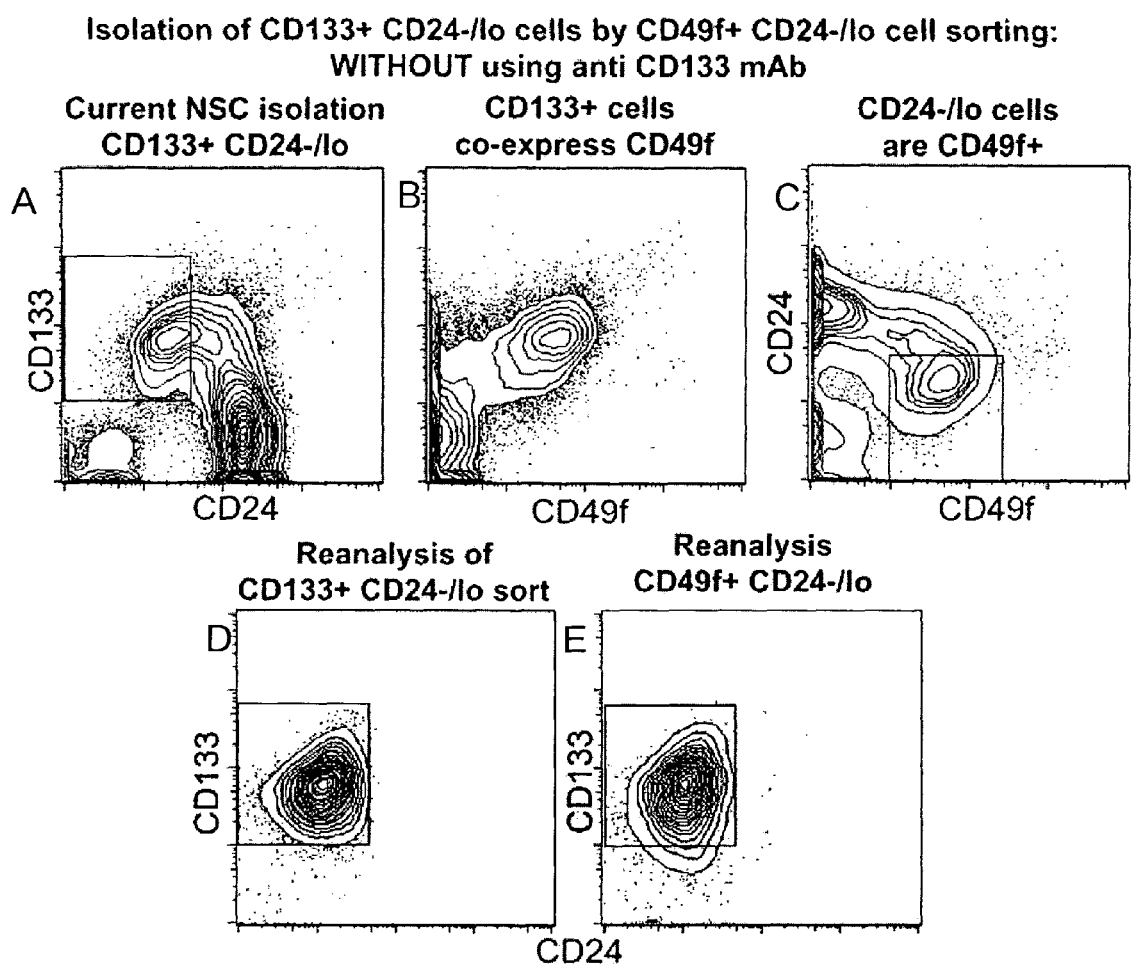

Figure 5 (Example 4)
The majority of Long-term neurosphere cells are CD133+ CD49f+
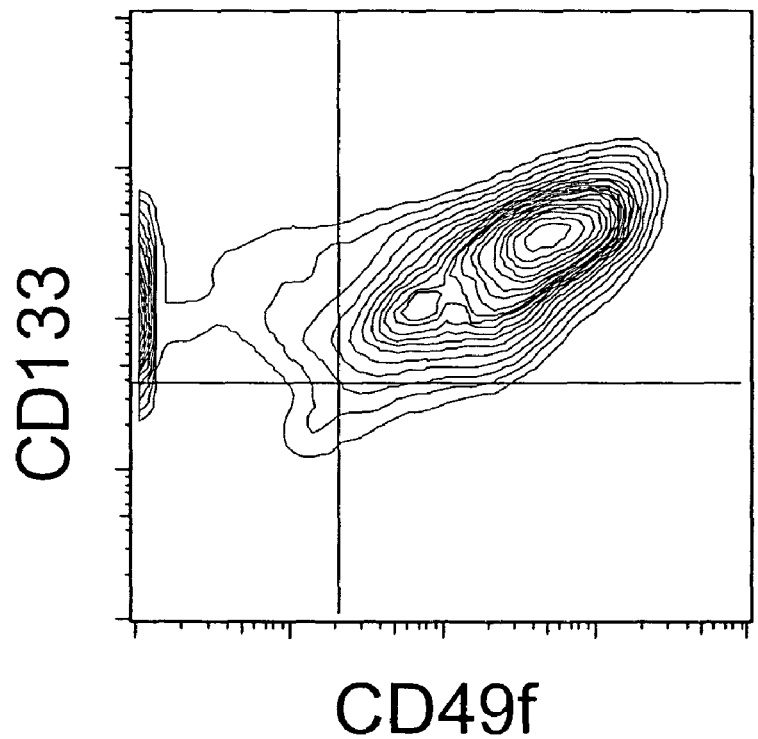

Figure 6 (Example 5)
Phenotypic analysis of human fetal brain cells
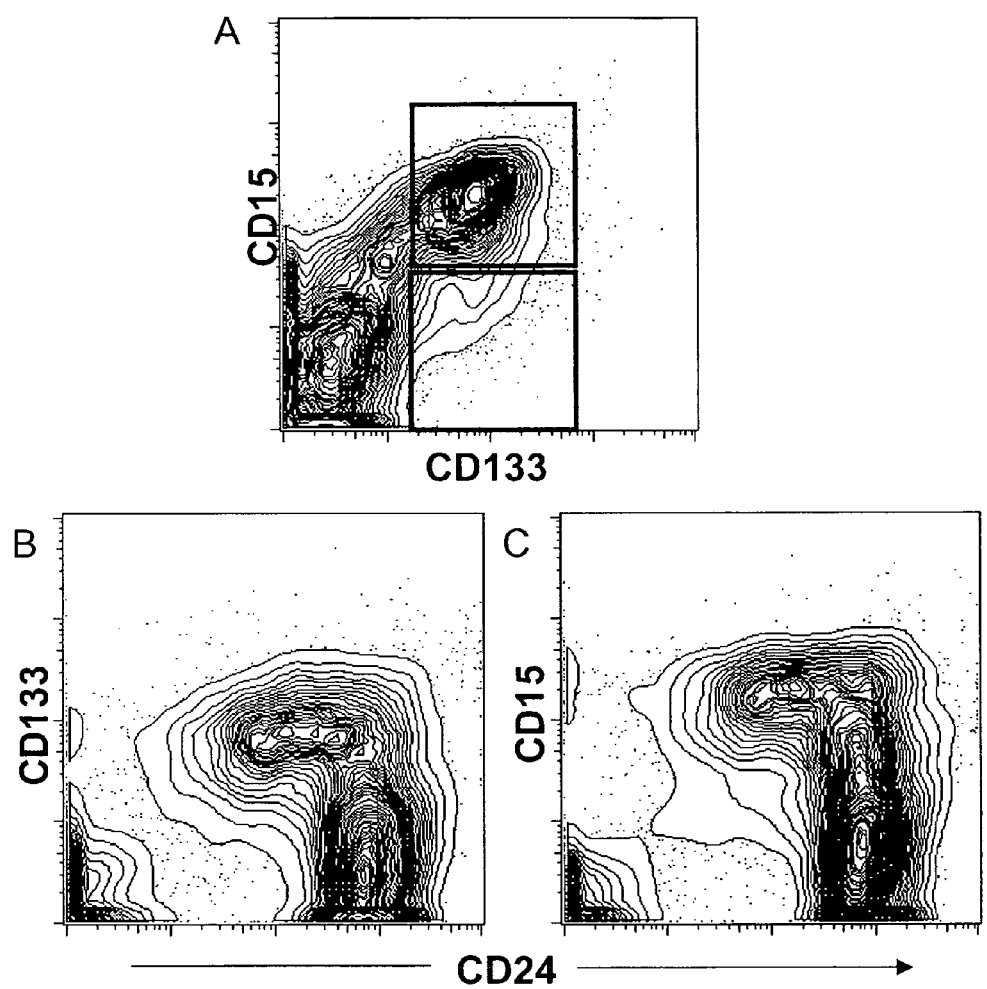
CD133$^+$ CD24$^{-/lo}$ = CD15$^{hi}$ CD24$^{-/lo}$ plus CD133$^+$ CD15$^{-/lo}$ CD24$^{-/lo}$ Figure 7 (Example 5)
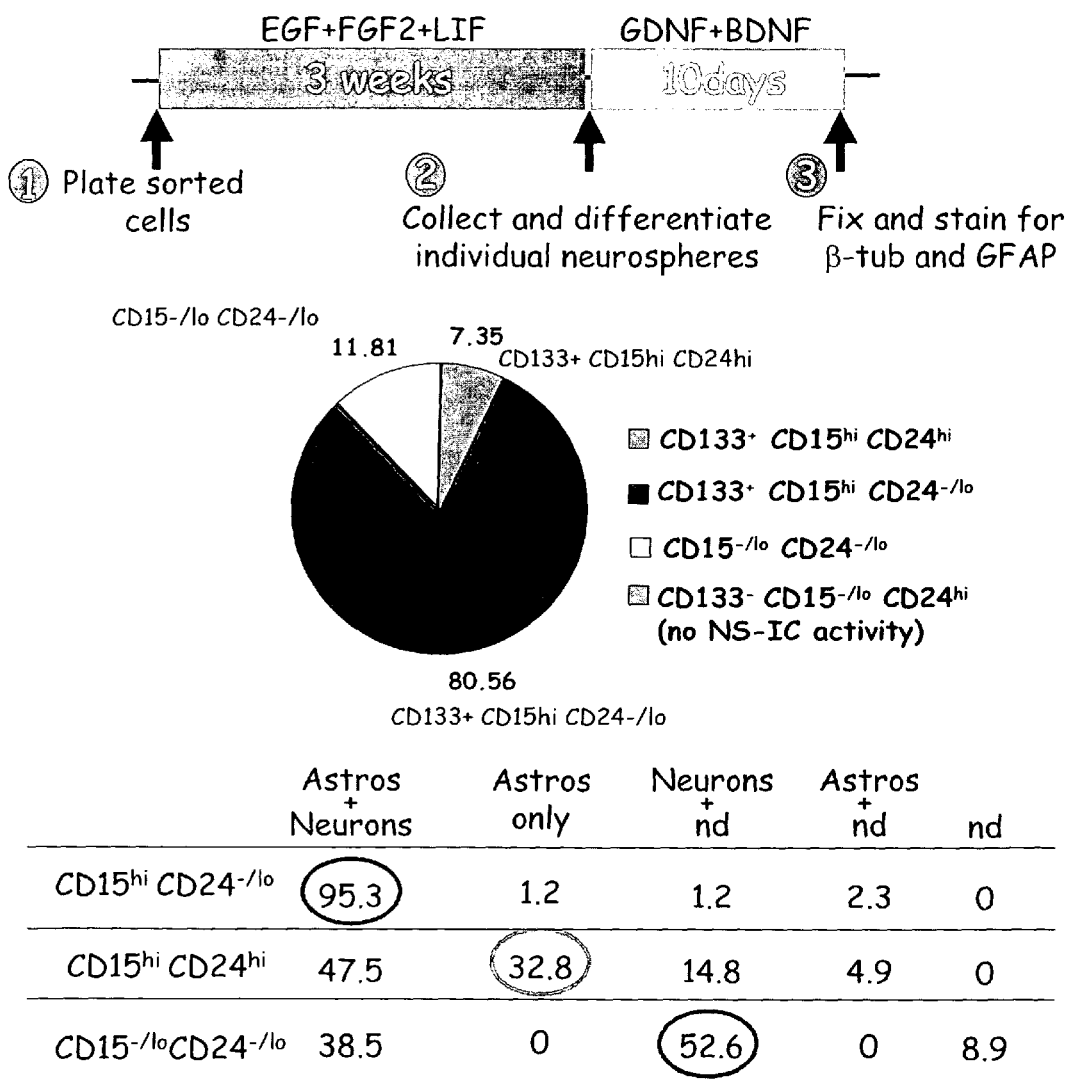

Figure 8 (Example 6)
A   CD133$^+$ CD15$^{-/lo}$ CD24$^{-/lo}$ sorted/expanded neurosphere cells, Olfactory bulb of 6 months post transplant NOD-Scid
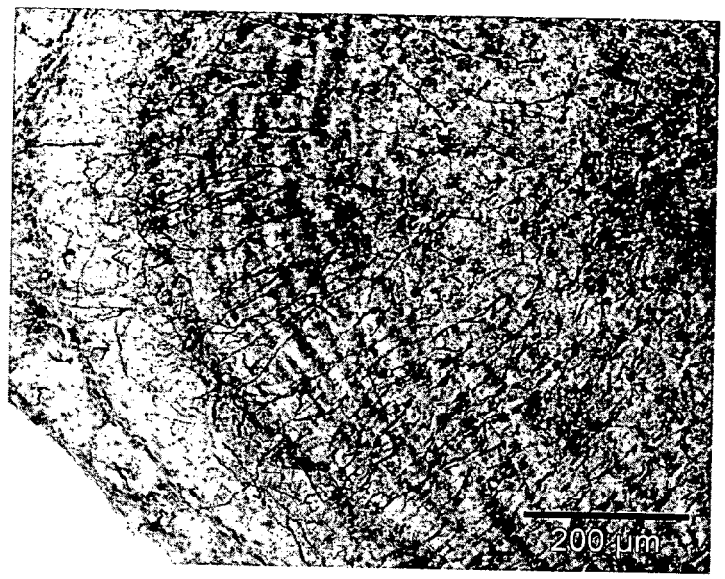
B   CD49f$^+$ CD24$^{-/lo}$ sorted/expanded neurosphere cells, Hippocampus of 6 months post transplant NOD-Scid
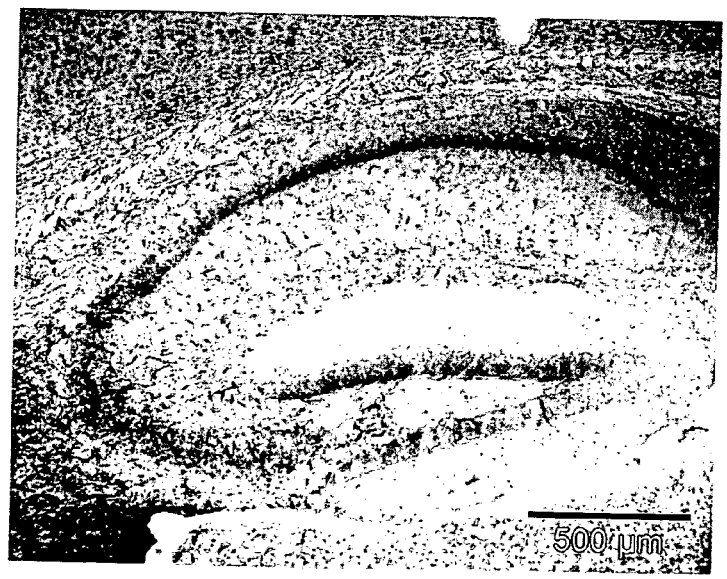

ENRICHED CENTRAL NERVOUS SYSTEM STEM CELL AND PROGENITOR CELL POPULATIONS, AND METHODS FOR IDENTIFYING, ISOLATING AND ENRICHING FOR SUCH POPULATIONS

RELATED APPLICATIONS

This application claims the benefit of U.S. Provisional Application No. 60/406,546, filed Aug. 27, 2002, the entire contents of which is hereby incorporated by reference.

TECHNICAL FIELD

This invention relates generally to enriched neural stem cell and progenitor cell populations, and methods for identifying, isolating and enriching for neural stem and progenitor cells, particularly central nervous system neural stem cells and progenitor cells, and most particularly to enriched populations of neurosphere initiating cells (NS-IC).

BACKGROUND OF THE INVENTION

Stem cell populations constitute only a small percentage of the total number of cells in the body, but are of immense interest because of their ability to repopulate the body. The longevity of stem cells and the dissemination of stem cell progeny are desirable characteristics. There is significant commercial interest in these methods because stem cells have a number of clinical uses. There is also medical interest in the use of stem cells as a vehicle for gene therapy.

Proteins and other cell surface markers found on stem cell and progenitor cell populations are useful in preparing reagents for the separation and isolation of these populations. Cell surface markers are also useful in the further characterization of these important cells.

Neural stem cells have been isolated from the adult subventricular zone (SVZ) and hippocampus (Gage, (2000) Science 287, 1433-38). These cells are an important source of new neurons, and offer the promise of novel central nervous system (CNS) repair therapies.

CNS stem cells are usually identified retrospectively by their ability to generate typical neurospheres or large adherent clones containing multiple neural cell types (Reynolds and Weiss, (1992) Science 255, 1707-10; Davis and Temple, (1994) Nature 372, 263-266; and Palmer et al., (1997) Mol. Cell. Neurosci. 8, 389-404), which precludes study of the initial stem cell population. Little is known about the unique biology of CNS stem cells, for example which specific gene products they express. Identification of "unique" gene products expressed by CNS stem cells would expand the understanding of these important cells, aid in their identification in vivo and enable their positive enrichment in vitro for study and use.

Two different cell populations have recently been identified as including SVZ stem cells: GFAP-expressing astrocytes (Doetsch et al., (1999) Cell 97 703-16; Doetsch et al., (1999) Proc. Natl. Acad. Sci. USA 96, 11619-11624) and Notch 1-expressing, ciliated ependymal cells lining the ventricles (Johansson et al., (1999) Cell 96, 25-34). These two distinct cell types are so intimately localized in vivo that it is difficult to separate them physically. Instead, defining specific features of stem cells will provide markers to help reveal their in vivo identity.

Genes expressed by adult CNS stem cells include Nestin, Musashi, Notch1 and GFAP (Sakakibara et al., (1996) Devel Biol. 176, 230-42; Johansson et al., (1999) Cell 96, 25-34; Doetsch et al., (1999) Cell 97, 703-16), but other CNS cell types also express these. Moreover, many of these markers are intracellular, limiting their usefulness for stem cell enrichment, although this problem can be overcome by creating transgenic mice with fluorescent reporter gene expression (Kawaguchi et al., (2001) Mol. Cell. Neurosci. 17, 259-273). A more generally useful marker would be a cell surface molecule allowing stem cell localization and purification from a wild-type mouse. Thus, there remains a need for tools, such as monoclonal antibodies that are useful in isolating and characterizing human non-hematopoietic progenitor and stem cells, and particularly central nervous system (CNS) neural stem cells and progenitor cells.

SUMMARY OF THE INVENTION

This invention provides methods for identifying, isolating, and enriching for human non-hematopoietic progenitor and stem cells, and particularly central nervous system (CNS) neural stem cells, progenitors, or combinations thereof which can initiate long-term neurospheres. The invention also provides for enriched populations containing CNS neural stem cells that can initiate neurospheres, and progenitor cells. As used herein, the term "neurosphere initiating cell (NS-IC)" refers to a cell that can initiate a long-term neurosphere culture. Those skilled in the art will recognize the NS-IC include stem cells or progenitors or a combination thereof, depending on the culture conditions used. A "neurosphere", in turn, is an aggregate or cluster of cells which includes neural stem cells and primitive progenitors. The identification, culture, growth, and use of neurospheres is disclosed in Weiss et al., U.S. Pat. No. 5,750,376 and Weiss et al., U.S. Pat. No. 5,851,832, both incorporated herein by reference. While the term "NS-IC" is defined by the ability or capacity of that cell to form a neurosphere, these cells may also be appropriately grown in adherent culture (see, for example, Johe, U.S. Pat. No. 5,753,506, and Weiss, U.S. Pat. No. 5,750,376, which are both incorporated herein by reference). The methods and populations described herein are not to be limited to suspension cultures of NS-IC. A NS-IC is nestin$^+$ and has the capability to differentiate, under appropriate differentiating conditions, to neurons, astrocytes, and oligodendrocytes.

Enriched populations of non-hematopoietic stem cells and progenitor cells, preferably CNS neural stem cells and/or progenitors including NS-ICs, and methods of identifying, isolating, or enriching for such cells, are achieved by contacting a population of cells containing at least one stem cell or NS-IC or progenitor cell with a reagent that binds to a surface marker glycoprotein antigen ("CD49f antigen") recognized by an antibody that specifically binds to CD49f ("anti-CD49f antibody") or to a cell surface carbohydrate moiety ("CD15 antigen") recognized by an antibody that specifically binds to CD15 ("anti-CD15 antibody"). As used herein, the term "reagent" is meant to include any composition or compound that is capable of binding to, associating with, or recognizing an antigen. Examples of such reagents include, but are not limited to monoclonal antibodies, polyclonal antibodies, small molecules, receptors, ligands, proteins, protein fragments, polypeptides, polypeptide fragments, nucleic acids, nucleic acid fragments, antibody fragments, and any other "reagents" known to those skilled in the art.

While the methods described herein refer to the use of the CD49f antigen to enrich populations of neural cells for NS-IC, other cell surface markers found on CNS-SC may also be used. Examples of such cell surface markers include, but are not limited to, the CD133 antigen, which is recognized by anti-CD133 monoclonal antibodies such as monoclonal antibody AC133, and CD15, which is recognized by anti-CD15 monoclonal antibodies including, but not limited to MMA. Those skilled in the art will recognize that any of the methods described herein using the CD49f antigen and/or the anti-CD49f antibody may also be accomplished in conjunction with antibodies and/or antigens that recognize CD133 and/or CD15 antibodies and/or antigens. Those skilled in the art will also recognize that any other cell-surface marker present on neural stem cells, progenitors, or NS-IC can also be used in the methods of the instant invention. Moreover, the skilled artisan will recognize that any combination of CD49f, CD133 and/or CD15 antibodies and/or antigens can be used to produce populations enriched for NS-IC. Those skilled in the art will also recognize that any reference to anti-CD133, anti-CD15 and/or anti-CD49f antibodies encompasses human, murine, rat, sheep, equine, goat, chicken, rabbit, guinea pig, and/or porcine antibodies.

The enriched populations of the invention may also be achieved by contacting a population of cells containing at least one stem cell or NS-IC or progenitor with a reagent that binds to the CD133 antigen including, but not limited to, the AC133 antibody. The contacting may be done before, during, and/or after the contacting with a reagent that binds to CD49f (e.g., an anti-CD49f antibody) or to CD15 (e.g., an anti-CD15 antibody). Antibodies to CD133 include, for example, monoclonal antibody AC133. As used herein, the terms "CD133 antibody" and "CD133 monoclonal antibody" encompass antibodies including, but not limited to AC133, that recognize the CD133 antigen. Moreover, CD133$^+$ cells are defined as cells containing the CD133 antigen.

In one preferred embodiment, the reagent is an anti-CD49f antibody (two such anti-CD49f antibodies are referred to herein as "GoH3" or "4F10"). In another preferred embodiment, the reagent is an anti-CD15 antibody (a preferred embodiment of anti-CD15 antibodies is referred to herein as MMA). Use of traditional techniques for cell sorting, such as by immunoselection (e.g., FACS), permits identification, isolation, and/or enrichment for cells in which contact between the reagent and the CD49f antigen or the CD15 antigen has been detected.

This invention also provides methods of using an antibody to provide enriched populations of non-hematopoietic stem cells and progenitor cells, preferably CNS neural stem cells that can initiate neurospheres and progenitor cells, and that may be used in methods of identifying, isolating, or enriching for such cells, by contacting a population of cells containing at least one stem cell, NS-IC or progenitor cell with an anti-CD49f antibody or with an anti-CD15 antibody.

The cells of this invention, preferably the CNS neural stem cells, are additionally characterized as lacking cell surface markers for CD45 and CD34 (e.g., CD45$^-$ and CD34$^-$).

This invention provides an antibody, herein called SC20, formerly known as 8G1 (Uchida, et al., PNAS 2000), which appears to recognize CD24 and permits subselection between populations of CNS neural stem cells (characterized as SC20$^{-/lo}$ or CD24$^{-/lo}$) and populations of CNS progenitor cells (characterized as SC20$^+$ or CD24$^{-/lo}$). CNS-SC isolated from fetal brains are CD133$^+$SC20$^{-/lo}$, which is also referred to as CD133$^+$CD24$^{-/lo}$. When CNS-SC are expanded in vitro as neurosphere cells, they may express CD24. Thus, the CD24 antigen appears to be upregulated as these cells proliferate. Therefore, neurosphere cells derived from CNS-SC are heterogeneous for CD24 expression (low to high levels). Other antibodies that recognize CD24 include 32D12 [Diatec, Oslo, NORWAY (catalog number CD24 3061-ab531)]; ALB9 [Accurate Chemical and Scientific Co., Westbury, N.Y.; BEK, Miami, Fla.; Biomeda Corporation, Foster City, Calif.; Biosource International, Camarillo, Calif. (catalog number AHS2402); Leinco Technologies, St. Louis, Mo. (catalog numbers C483; C484); Research Diagnostics, Inc., Flanders, N.J.]; CLB134 [Accurate Chemical and Scientific Co., Westbury, N.Y.; Cell Science, Norwood, Mass. (catalog number MON 1119)]; CLBGRANBLy1 [Accurate Chemical and Scientific Co., Westbury, N.Y.; Research Diagnostics, Inc., Flanders, N.J.]; SN3 [Caltag Laboratories, Inc., Burlingame, Calif. (catalog numbers MHCD2400; MHCD2401; MHCD2404)]; ML5 [BD Pharmingen, San Diego, Calif. (catalog numbers 555427; 555428; 555426)]; and 24C02 [Lab Vision Corporation, Freemont, Calif. (catalog number MS-1279); United States Biological, Swampscott, Mass.].

The invention involves methods for producing a population enriched for human CNS-SC and/or progenitors which can initiate neurospheres (NS-IC) by contacting neural or neural derived cells with a monoclonal antibody that binds to CD49f or with a monoclonal antibody that binds to CD15; selecting the cells that bind to this monoclonal antibody (e.g. CD49$^+$, CD15$^+$, and CD15$^{-/lo}$ cells); and optionally removing the bound cells, wherein the selected cells are enriched for human CNS-SC and/or progenitors and wherein the CD15$^{-/lo}$ cells are a subset of the CD133$^+$CD24$^{-/lo}$ cells. The population containing neural or neural-dervided cells may be obtained from a neurosphere culture or an adherent culture or from primary neural tissue. In the various embodiments of this invention, the monoclonal antibody may be fluorochrome conjugated or may be conjugated to magnetic particles. Additionally, the selecting may be by fluorescence activated cell sorting, high gradient magnetic selection, or by attachment to and disattachment from the solid phase.

The methods may also involve the step of further enriching the population obtained from primary neural tissue for CNS-SC and/or progenitors by contacting the removed cells with a second monoclonal antibody SC20 and eliminating those cells that are SC20$^+$ (CD24$^+$) or SC20$^{hi}$ (CD24$^{hi}$) to produce a population enriched for CNS-SC and/or progenitors, wherein the selected cells in the population are SC20$^{-/lo}$ (CD24$^{-/lo}$). Alternatively, the selected cells can be further selected for those cells at hat are SC20$^{-/lo}$ (CD24$^{-/lo}$).

The methods may also involve the step of further enriching the population for CNS-SC and/or progenitors by contacting the remaining cells with an anti-CD133 monoclonal antibody and selecting those cells that bind to the anti-CD133 monoclonal antibody to obtain a population enriched for CNS-SC and/or progenitors. Alternatively, the neural or neural-derived cells may be contacted with an anti-CD133 monoclonal antibody (e.g., AC133) prior to, during, or after contacting the cells with a monoclonal antibody that binds to CD49f or with a monoclonal antibody that binds to CD15. Throughout this specification, the term AntibodyX$^+$ is used interchangeably herein with the term AntibodyX$^{hi}$.

The invention involves methods for producing a population enriched for CNS-SC and/or progenitors, which can initiate neurospheres (NS-IC) or an adherent culture by selecting from a population of neural or neural-derived cells for cells that are CD49f$^+$. This may be accomplished by contacting the population with an anti-CD49f antibody, preferably, monoclonal antibody GoH3 or monoclonal antibody 4F10, and removing those cells that do not bind to monoclonal antibody GoH3 or monoclonal antibody 4F10. In one embodiment, the invention also provides a step for further enriching the population from primary neural tissues by removing the cells that are CD24$^+$ from the remaining population or by selecting for the cells that are CD2$^{-/lo}$. This may be done, for example, by selecting for cells that bind to monoclonal antibody SC20, which recognizes cells expressing high levels of CD24 (e.g. by removing the cells that bind to monoclonal antibody SC20, which recognizes CD24 (CD24$^+$ cells) or by selecting for cells that are CD24$^{-/lo}$). The remaining cells may be CD24$^{-/lo}$. Such methods can also involve the step of further enriching the population by selecting those cells that are CD133$^+$. Alternatively, the population of neural or neural-derived cells may be selected for CD133$^+$ cells prior to or concurrently with selecting for CD49f$^+$ cells. Cells that are CD15$^{hi}$ may be selected using monoclonal antibody MMA.

The invention involves methods for enriching from a population of neural cells for the populations of neurosphere initiating stem cells and/or progenitors (NS-IC) fraction by selecting from the neural cells for cells that bind to an anti-CD49f antibody, such as monoclonal antibody GoH3 or monoclonal antibody 4F10, (or to an anti-CD15 antibody such as monoclonal antibody MMA, e.g. cells that are CD15$^{-/lo}$ or CD15$^{hi}$, wherein the CD15$^{-/lo}$ cells are a subset of the CD133$^+$CD24$^{-/lo}$ population), wherein the selected cells are enriched in the fraction of NS-IC as compared with the population of neural cells. The fractions obtained from primary neural tissues can be further enriched by removing those cells that bind to an anti-CD24 antibody, such as monoclonal antibody SC20 (e.g., by removing those cells that are CD24$^+$ such that the remaining cells may be CD24$^{-/lo}$ or by selecting for cells that are CD24$^{-/lo}$). Additionally, the fraction can be further enriched by selecting for those cells that bind to an anti-CD133 antibody, such as monoclonal antibody AC133, those cells that bind to the anti-CD133 antibody, such as monoclonal antibody AC133 are selected prior to, during, or after selecting for those cells that bind to the anti-CD49f antibody, such as monoclonal antibody GoH3 or monoclonal antibody 4F10 (or to the anti-CD15 antibody, such as monoclonal antibody MMA).

The invention also provides methods for isolating a neurosphere initiating stem cell and/or progenitor cell (NS-IC) obtained from primary neural tissues, by selecting from a population of neural or neural-derived cells for cells that are CD49f$^+$ or that are CD15$^{hi}$ or CD15$^{-/lo}$, wherein the CD15$^{-/lo}$ cells are a subset of the CD133$^+$CD24$^{-/lo}$ cells; removing those cells that bind strongly to monoclonal antibody SC20 (i.e., SC20$^+$ cells, wherein the remaining cells are CD24$^{-/lo}$ cells); introducing the remaining cells to a serum-free culture medium containing one or more growth factors selected from the group consisting of LIF, EGF, bFGF, and combinations thereof; and proliferating the remaining cells in the culture medium. The selected cells may be further enriched by selecting for cells that are CD133$^+$. This further enrichment step may be accomplished either before, during, or after selecting for cells that are CD49f$^+$, CD15$^+$, or CD15$^{-/lo}$.

Antibodies that specifically bind to the CD49f antigen are also provided, wherein the CD49f antigen specifically binds to the GoH3 antibody or the 4F10 antibody. This antibody may be produced by a hybridoma cell line. In some embodiments, this antibody may block simultaneous binding to the CD49f antigen by the antibody GoH3 and/or the 4F10 antibody.

Also provided are antibodies that specifically bind to the CD15 antigen, wherein the CD15 antigen specifically binds to the MMA antibody. This antibody may be produced by a hybridoma cell line. In some embodiments, this antibody may block simultaneous binding to the CD15 antigen by the antibody MMA.

Also provided is a method for the enrichment of human CNS-SC and/or progenitors which can initiate neurospheres (NS-IC) by combining a population of neural or neural-derived cells with a reagent that specifically binds to the CD49f antigen and/or to the CD15 antigen and selecting for those cells that bind to the CD49f reagent or the CD15 reagent, wherein the selected cells (CD49f$^+$, CD15$^{hi}$, or CD15$^{-/lo}$, wherein the CD15$^{-/lo}$ cells are a subset of the CD133$^{-/lo}$ cells) are enriched for NS-IC. The reagent may include at least one antibody, and the at least one antibody may be fluorochrome conjugated, wherein the selecting is accomplished by flow cytometry. Alternatively, the at least one antibody may be conjugated to magnetic particles, wherein the selecting is by high gradient magnetic selection. Such methods further involve the step of further enriching the population by combining the selected cells with a second reagent that specifically binds to the CD133 antigen and selecting for those cells that bind to the second reagent. The population of neural or neural-derived cells may be selected for cells that bind to a reagent that specifically binds to the CD133 antigen prior to, during, or following selecting for those cells that bind to a reagent that specifically binds to the CD49f antigen or to the CD15 antigen.

In any of the methods described herein, the population of cells can be further enriched for CNS-SC by either selecting for cells that are CD24$^{-/lo}$ or by removing cells that are CD24$^+$ from the population, such that the remaining cells are CD24$^{-/lo}$.

Methods for producing a population enriched for human CNS-SC and/or progenitors, which can initiate neurospheres (NS-IC) by selecting from a population of neural or neural derived cells for cells that are CD49f$^+$ or for cells that are CD15$^+$or CD15$^{-/lo}$, wherein the CD15$^{-/lo}$ cells are a subset of the CD133$^+$CD24$^{-/lo}$ cells, are also provided.

Moreover, methods for producing a population enriched for human CNS-SC and/or progenitors which can initiate neurospheres (NS-IC) by selecting from neural or neural-derived cells for cells that bind to an anti-CD49f antibody, such as monoclonal antibody GoH3 or to monoclonal antibody 4F10, to produce a population enriched for CNS-SC, wherein the selecting is achieved by attachment to and disattachment from a solid phase. The population may be further enriched by selecting cells that bind to an anti-CD133 antibody, such as monoclonal antibody AC133. Additionally, the population may be further enriched by selecting for cells that bind to the anti-CD133 antibody (e.g. AC133) prior to, during, or after selecting for cells that bind to an anti-CD49f antibody, such as monoclonal antibodies GoH3 or 4F10.

The invention involves methods for producing a population enriched for human CNS-SC and/or progenitors which can initiate neurospheres (NS-IC) by selecting from neural or neural-derived cells for cells that bind to monoclonal antibody MMA, which recognizes the CD15 antigen (e.g. CD15$^{hi}$ or CD15$^{-/lo}$ cells, wherein the CD15$^{-/lo}$ cells are a subset of the CD133$^+$CD24$^{-/lo}$ cells), to produce a population enriched for CNS-SC, wherein the selecting is achieved by attachment to and disattachment from a solid phase. The population may be further enriched by selecting cells that bind to an anti-CD133 antibody, such as monoclonal antibody AC133. Additionally, the population may be further enriched by selecting for cells that bind to an anti-CD133 antibody, such as monoclonal antibody AC133 prior to, during, or following selecting for cells that bind to a CD15 antibody, such as monoclonal antibody MMA.

Moreover, the invention provides methods for isolating a subset of human central nervous system progenitor cells by contacting neural or neural derived cells with a monoclonal antibody that binds to CD15 and selecting the neural or neural derived cells that bind to the monoclonal antibody (e.g. selecting for $CD15^{hi}$ or $CD15^{-/lo}$ cells, wherein the $CD15^{-/lo}$ cells are a subset of the $CD133^+CD24^{-/lo}$ cells) and optionally removing the bound cells (or the unbound cells), wherein the selected cells are a subset of human central nervous system progenitor cells that are selected from the group consisting of neuronal progenitors and glial progenitors. For example, the antibody may be monoclonal antibody MMA.

Finally, the invention involves methods for isolating a subset of human central nervous system progenitor cells by selecting from a population of neural or neural derived cells for those cells that are $CD15^+$ or $CD15^{-/lo}$, wherein the $CD15^{-/lo}$ cells are a subset of the $CD133^+CD24^{-/lo}$ cells and wherein the selected cells are a subset of human central nervous system progenitor cells that are selected from the group consisting of neuronal progenitors and glial progenitors.

Unless otherwise defined, all technical and scientific terms used herein have the same meaning as commonly understood by one of ordinary skill in the art to which this invention belongs. Although methods and materials similar or equivalent to those described herein can be used in the practice of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only not intended to be limiting. Other features and advantages of the invention will be apparent from the following detailed description and claims.

BRIEF DESCRIPTION OF THE DRAWINGS

FIG. 3 is a dot plot of FACS sorting data showing the isolation of human neural stem cells by cell surface markers. The figure shows that NS-IC typically express negative to low levels of CD24 antigen for the SC20 (8G1) antibody. Since NS-IC expressed low levels of CD133 antigens, signals for CD133 detection was amplified in multi-step staining methods.

FIG. 4 is a dot plot of fluorescence activated cell sorting (FACS) data showing the isolation of human CNS neural stem cells using cell surface markers using monoclonal antibodies to CD49f alone or in conjunction with antibodies that recognize CD24. In Panel A, the x axis represents cells staining for antibodies to CD24, and the y axis represents cells staining for antibodies to CD133. In Panel B, the x axis represents cells staining for antibodies to CD49f, and the y axis represents cells staining for antibodies to CD133. In Panel C, the x axis represents cells staining for antibodies to CD49f, and the y axis represents cells staining for antibodies to CD24. In Panels D and E, the x axis represents cells staining for antibodies to CD24 and the y axis represents cells staining for antibodies to CD133.

FIG. 5 is a series of dot plots of fluorescence activated cell sorting (FACS) data showing the isolation of human CNS stem cells using cell surface markers using monoclonal antibodies to CD133 alone or in conjunction with antibodies that recognize CD49f, which shows that the majority of long-term neurosphere cells are $CD133^+CD49f^+$, the x axis represents cells staining for antibodies to CD49f and the y axis represents cells staining for antibodies to CD133.

FIG. 6 is a series of dot plots of fluorescence activated cell sorting (FACS) data showing the phenotypic analysis of human fetal brain cells. In Panel A, the x axis represents cells staining for antibodies to CD133 and the y axis represents cells staining for antibodies to CD15. In Panel B, the x axis represents cells staining for antibodies to CD24 and the y axis represents cells staining for antibodies to CD15. The area of detail represents a limiting dilution of $CD15^+CD24^{-/lo}$ cells of 1 in 4.5 (22.5%). In Panel C, the x axis represents cells staining for antibodies to CD24 and the y axis represents cells staining for antibodies to CD133. As shown in Panels B and C, $CD133^+CD24^{-/lo}$ cells consist of $CD15^{hi}CD24^{-/lo}$ and $CD133^+CD15^{-/lo}CD24^{-/lo}$ cells.

FIG. 7 is a diagram showing that CD15 expression defines different subsets of expandable CNS stem cells and progenitors. Panel A shows a schematic diagram of experimental design. Panel B shows the proportion of NS-IC activity in different subsets. 80.56%, 11.81%, and 7.35% of neurospheres were derived from the $CD133^+CD15^+CD24^{-/lo}$, $CD133^+CD15^{-/lo}CD24^{-/lo}$, and $CD133^+CD15^+CD24^+$ subsets, respectively.

FIG. 8 shows the immunohistochemistry of NOD-Scid brain engrafted with $CD133^+CD15^{-/lo}CD24^{-/lo}$ sorted/expanded neurosphere cells in the olfactory bulb (A) and $CD49f^+CD24^{-/lo}$ sorted/expanded neurosphere cells in the hippocampus (B). Neurosphere cells were transplanted into the lateral ventricles of neonatal NOD-Scid and grafts were harvested 6 months after transplantation.

DETAILED DESCRIPTION OF THE INVENTION

A population of cells exists within the adult central nervous system (CNS), which exhibit stem cell properties. They have the ability to self-renew and to produce the differentiated mature cell phenotypes of the adult CNS. These stem cells are found throughout the CNS, and particularly in the subventricular regions, and dentate gyrus of the hippocampus.

Growth factor-responsive stem cells can be isolated from many regions of the neuraxis and at different stages of development, of murine, rodent and human CNS tissue. These cells vary in their response to growth factors such as EGF, basic FGF (bFGF, FGF-2) and transforming growth factor alpha (TGFα), and can be maintained and expanded in culture in an undifferentiated state for long periods of time. Both adult and embryonic murine progenitor cells respond to EGF and grow as spheres of undifferentiated cells. These cells show the characteristics of stem cells in that they are multipotent, and under serum containing conditions can differentiate into neurons, astrocytes and oligodendrocytes, as well as maintaining a subpopulation, which remains undifferentiated and continues to proliferate under EGF administration. Murine EGF-responsive progenitor cells express mRNA for the EGF receptor in vitro. Human CNS neural stem cell cultures have also been identified. The identification, culture, growth, and use of mammalian, including human, neural stem cell cultures, either as suspension cultures or as adherent cultures, is disclosed in Weiss et al., U.S. Pat. No. 5,750,376 and Weiss et al., U.S. Pat. No. 5,851,832, both incorporated herein by reference. Similarly, Johe, U.S. Pat. No. 5,753,506, also incorporated herein by reference, refers to adherent CNS neural stem cell cultures. When cultured in suspension, CNS neural stem cell cultures typically form neurospheres.

Figure 1:
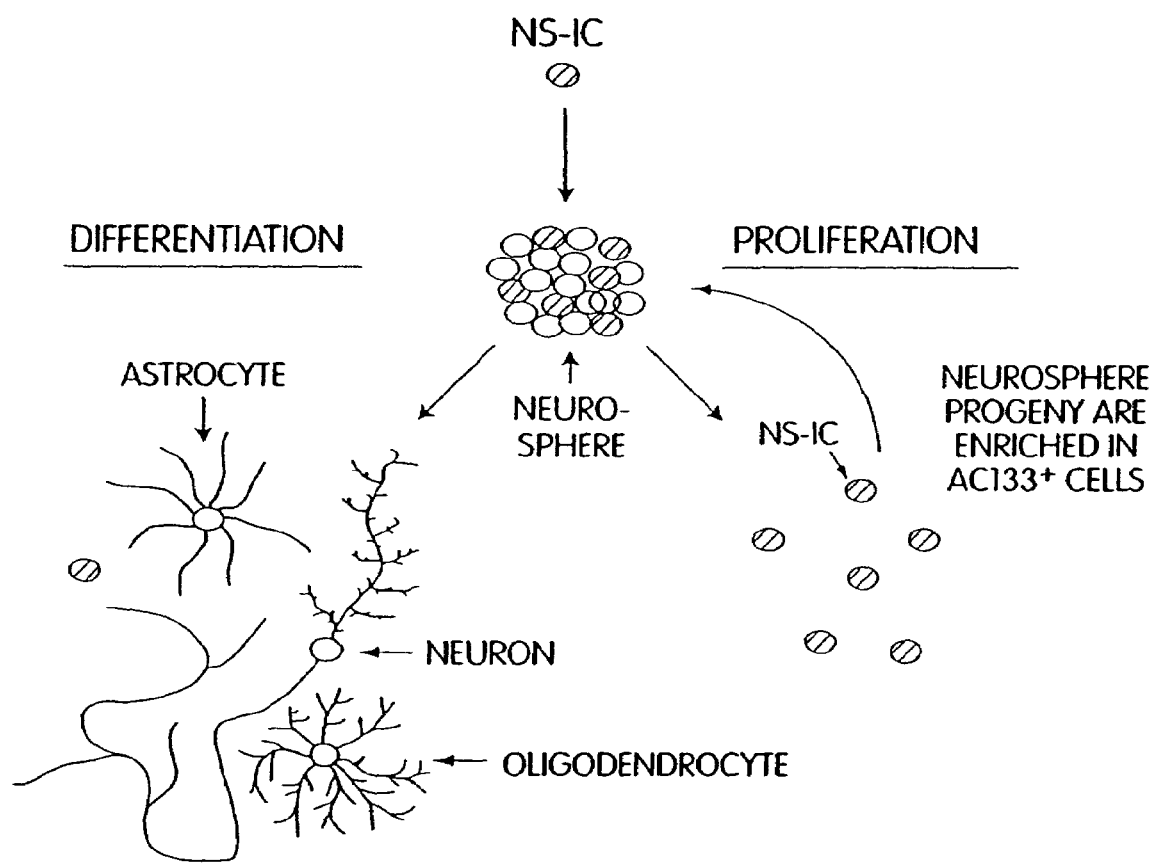
FIG. 1 is a diagram illustrating the proliferation and differentiation of a NS-IC.
Figure 2:
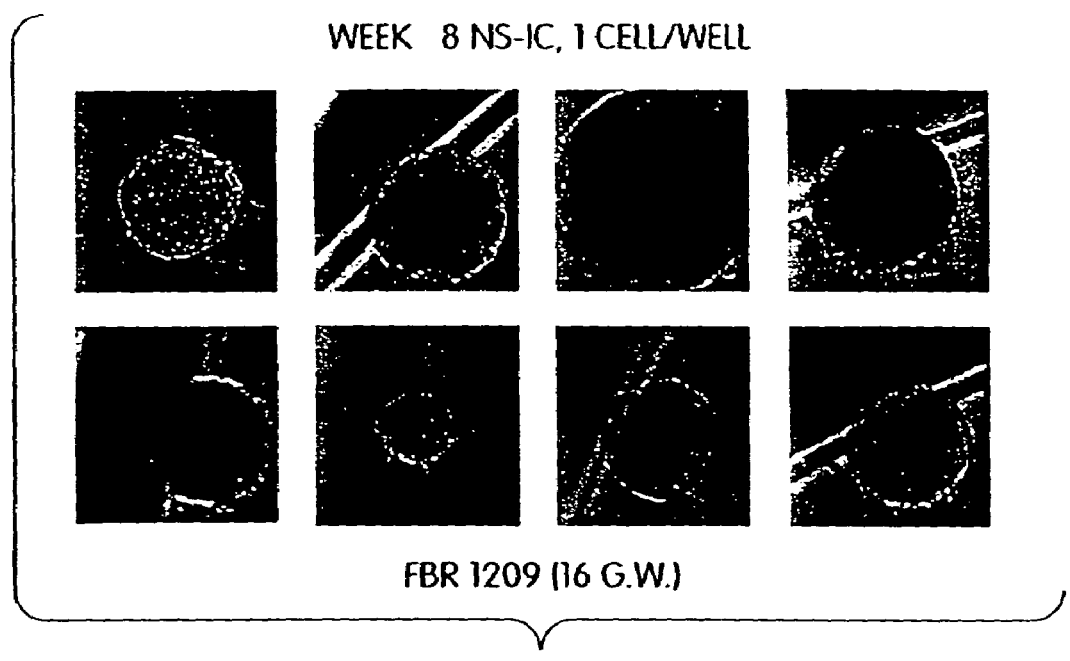
FIG. 2 is a series of photographs showing that neurosphere cultures can be initiated from single-cell sorted $CD133^+$ cells.

FIG. 1 shows the proliferation of a NS-IC as it develops into a neurosphere, and the subsequent differentiation into neuronal and glial phenotypes, as well as the generation of a progeny NS-IC. In the presence of one or more proliferation-inducing growth factors, the NS-IC divides and gives rise to a sphere of undifferentiated cells composed of more stem cells and progenitor cells (a "neurosphere"). When the clonally derived neurosphere is dissociated and plated as single cells in the presence of one or more proliferation-inducing growth factors, each NS-IC can generate a new neurosphere. The cells of a single neurosphere are clonal in nature because they are the progeny of a single neural stem cell. In the continued presence of a proliferation-inducing growth factor such as EGF or the like, precursor cells within the neurosphere continue to divide resulting in an increase in the size of the neurosphere and the number of undifferentiated neural cells. The neurosphere is not immunoreactive for neurofilament (NF; a marker for neurons), neuron-specific enolase (NSE; a marker for neurons), glial fibrillary acidic protein (GFAP; a marker for astrocytes), or myelin basic protein (MBP; a marker for oligodendrocytes). However, cells within the neurosphere are immunoreactive for nestin, an intermediate filament protein found in many types of undifferentiated CNS cells (Lehndahl et al., 60 CELL 585-595 (1990), incorporated herein by reference). Antibodies are available to identify nestin, including the rat antibody referred to as Rat401. If the neurospheres are cultured in conditions that allow differentiation, the progenitor cells differentiate to neurons, astrocytes and oligodendrocytes. The mature phenotypes associated with the differentiated cell types that may be derived from the neural stem cell progeny are predominantly negative for the nestin phenotype.

The terminology used for undifferentiated, multipotent, self-renewing, neural cells has evolved such that these cells are now termed "neural stem cells." A neural stem cell is a clonogenic multipotent stem cell, which is able to divide and, under appropriate conditions, has self-renewal capability for NS-IC and can include in its progeny daughter cells, which can terminally differentiate into neurons, astrocytes, and oligodendrocytes. Hence, the neural stem cell is "multipotent" because stem cell progeny have multiple differentiation pathways. A neural stem cell is capable of self-maintenance, meaning that with each cell division, one daughter cell will also be on average a stem cell.

The non-stem cell progeny of a neural stem cell are typically referred to as "progenitor" cells, which are capable of giving rise to various cell types within one or more lineages. The term "neural progenitor cell" refers to an undifferentiated cell derived from a neural stem cell, and is not itself a stem cell. Some progenitor cells can produce progeny that are capable of differentiating into more than one cell type. For example, an O-2A cell is a glial progenitor cell that gives rise to oligodendrocytes and type II astrocytes, and thus could be termed a "bipotential" progenitor cell. A distinguishing feature of a progenitor cell is that, unlike a stem cell, it does not exhibit self maintenance, and, typically, is thought to be committed to a particular path of differentiation and will, under appropriate conditions, eventually differentiate into glia or neurons.

As used herein, the term "precursor cells" refers to the progeny of neural stem cells, and thus includes both progenitor cells and daughter neural stem cells.

Cell markers. This invention provides for the identification, isolation, enrichment, and culture of neural stem cells and/or progenitors that are capable of forming neurospheres (NS-IC). NS-ICs are identified or selected through the binding of antigens, found on the surfaces of NS-ICs, to reagents that specifically bind the cell surface antigen.

In order to normalize the distribution to a control, each cell is recorded as a data point having a particular intensity of staining. These data points may be displayed according to a log scale, where the unit of measure is arbitrary staining intensity. In one example, the brightest cells in a population are designated as 3 logs more intense than the cells having the lowest level of staining. When displayed in this manner, it is clear that the cells falling in the highest log of staining intensity are bright, while those in the lowest intensity are negative. The "low" staining cells, which fall in the 2-3 log of staining intensity, may have properties that are unique from the negative and positive cells. An alternative control may utilize a substrate having a defined density of marker on its surface, for example a fabricated bead or cell line, which provides the positive control for intensity. The "low" designation indicates that the level of staining is above the brightness of an isotype-matched control, but is not as intense as the most brightly staining cells normally found in the population.

As used herein, the terms $CD15^{lo}$ and/or $CD15^{low}$ and/or $CD15^{-/lo}$ refer to "low" staining cells, which fall into the $1^{st}$-$2^{nd}$ log of staining intensity. When the few molecules (<100-500) in a given antigen were expressed on the cell surface, the signal to noise ratio may be poor to determine whether a given antigen is expressed on the cell surface. Those skilled in the relevant arts will recognize that any of the antibodies described herein can also be described using the "lo" or "low" designation (i.e. antibody$X^{lo}$ or antibody$X^{low}$), without altering the intended meaning. Likewise, as used herein, the terms $CD15^{hi}$, $CD15^{high}$, and/or $CD15^{bright}$ refer to those cells in the population designated as 3 logs more intense than the cells having the lowest level of staining. Again, those skilled in the art will recognize that any antibody can be described using these designations, without altering the intended meaning (i.e., antibody$X^{hi}$, antibody$X^{high}$, or antibody$X^{bright}$). The designation antibody$X^{med}$ is intended to refer to an antibody having a staining intensity falling between "low" and "bright". Moreover, as used herein, the designations antibody$X^+$ and antibody$X^{hi}$ are used interchangeably.

One of the antigens found on the surface of NS-IC is an antigen that binds to the AC133 monoclonal antibody (i.e., the CD133 antigen). Yin et al., U.S. Pat. No. 5,843,633, incorporated herein by reference, describes a monoclonal antibody called AC133, which binds to a surface marker glycoprotein on hematopoietic stem and progenitor cells. The AC133 antigen (also referred to herein as the "CD133 antigen" or "CD133") is a 5-transmembrane cell surface antigen with a molecular weight of 117 kDa. Expression of this antigen is highly tissue specific, and has been detected on a subset of hematopoietic progenitor cells derived from human bone marrow, fetal bone marrow and liver, cord blood, and adult peripheral blood. The subset of cells recognized by the AC133 antibody is $CD34^{bright}$, and contains substantially all of the CFU-GM activity present in the $CD34^+$ population, making AC133 useful as a reagent for isolating and characterizing human hematopoietic progenitor and stem cells.

The AC133 antibody (also referred to herein as the 5F3 antibody) is exemplary of antibody embodiments of reagents that recognize a human cell marker termed prominin. Prominin is a polytopic membrane protein expressed in various epithelial cells (Weigmann et al., 94(23) Proc Natl Acad Sci U S A. 12425-30 (1997); Corbeil et al., 112 (Pt 7) J Cell Sci. 1023-33 (1999); Corbeil et al., 91(7) Blood 2625-6 (1998); Miriglia et al., 91(11) Blood 4390-1 (1998)). Various AC133 antibodies are described in U.S. Pat. No. 5,843,633, which is incorporated herein by reference. A deposit of the murine hybridoma cell line AC133 was made at the American Type Tissue Collection, 12301 Parklawn Drive, Rockville Md. 20852, on Apr. 24, 1997, and given the ATCC designation HB12346. These AC133 antibodies are capable of immunoselection for a subset of human cells of interest in this invention. Preferred AC133 monoclonal antibodies can be obtained commercially from Miltenyi Biotec Inc. (Auburn Calif.), including, but not limited to, AC133/1-PE antibody (Cat #808-01) and AC133/2-PE antibody (Cat #809-01). For MACS separation, a 50:50 mixture of the monoclonal antibodies is preferred. The high tissue specificity of AC133 expression is particularly advantageous during enrichment for highly purified NS-IC populations. A discussion of the use of the AC133 antigen to select NS-IC is found in U.S. Pat. No. 6,468,794, which is incorporated herein by reference.

"Anti-CD133 antibodies" are characterized by binding to the CD133 protein in native, in FACS and immunoprecipitation experiments, as well as denatured, in western blot experiments, conformation. The CD133 antigen has been reported to have several reduced molecular weights in the range of 125 kDa to 127 kDa according to U.S. Pat. No. 5,843,633 and 115 kDa to 127 kDa according to United States Published Patent Application No. 20010051372. Examples of anti-CD133 antibodies include, but are not limited to, AC133 and SC111 (StemCells, Inc., Palo Alto, Calif.).

CD45 is the T200/leucocyte common antigen. Antibodies to CD45 are commercially available from, e.g. Miltenyi Biotec (Auburn, Calif.) (catalog numbers 130-080-201; 130-080-202); and Research Diagnostics (Flanders, N.J.) (catalog numbers RDI-M1343clb; RDI-CBL124; RDI-CBL148; RDI-CBL464, etc.). In a preferred embodiment, the cells of this invention and cultures containing them, are additionally characterized (in addition to being prominin positive) as lacking cell surface markers such as CD45.

CD34 is also known as gp105-120. Monoclonal antibodies to CD34 are commercially available from, e.g., Miltenyi Biotec (Auburn, Calif.) (catalog numbers 130-090-954); Research Diagnostics (Flanders, N.J.) (catalog numbers RDI-M1636clb; RDI-CBL128; RDI-CBL496FT; RDI-M228clb; RDI-CD34-581, etc.); BD Biosciences, Pharmingen (San Diego, Calif.) (catalog number 550760)). Anti-CD34 monoclonal antibodies have been used to quantify and purify lymphohematopoietic stem/progenitor cells for research and for clinical bone marrow transplantation. CD34 is a monomeric cell surface antigen with a molecular mass of approximately 110 kDa that is selectively expressed on human progenitor cells. The gene is expressed by small vessel endothelial cells in addition to hematopoietic progenitor cells and is a single-chain 105-120 kDa heavily O-gylcosylated transmembrane glycoprotein. The sequence is disclosed by Simons et al. (1992) J. Immun. 148:267-271.

The monoclonal antibody SC20, formerly known as 8G1 (Uchida et al., PNAS 2000) is believed to recognize CD24. It specifically reacts with the 515 kilodalton α-chain of human LRP/A2MR which is expressed in a restricted spectrum of cell types. A strong immunohistochemical reaction is seen in hepatocytes, tissue macrophages, subsets of neurons and astrocytes in the central nervous system, fibroblasts, smooth muscle cells, and monocyte-derived foam cells in atherosclerotic lesions in the arterial wall. This antibody can also be used for the characterization of a subset of myelomonocytic subtypes of chronic and acute leukemia (CD91). Antibodies to CD91 are commercially available from, e.g., Research Diagnostics (Flanders, N.J.) (catalog numbers RDI-PRO651102; RDI-PRO610102; RDI-PRO61065, etc.).

Other examples of antibodies that recognize CD24 include 32D12 [Diatec, Oslo, NORWAY (catalog number CD24 3061-ab531)]; ALB9 [Accurate Chemical and Scientific Co., Westbury, N.Y.; BEK, Miami, Fla.; Biomeda Corporation, Foster City, Calif.; Biosource International, Camarillo, Calif. (catalog number AHS2402); Leinco Technologies, St. Louis, Mo. (catalog numbers C483; C484); Research Diagnostics, Inc., Flanders, N.J.]; CLB134 [Accurate Chemical and Scientific Co, Westbury, N.Y.; Cell Sciences, Norwood, Mass. (catalog number MON 1119)]; CLBGRANBLy1 [Accurate Chemical and Scientific Co., Westbury, N.Y.; Research Diagnostics, Inc., Flanders, N.J.]; SN3 [Caltag Laboratories, Inc., Burlingame, Calif. (catalog numbers MHCD2400; MHCD2401; MHCD2404)]; ML5 [BD Pharmingen, San Diego, Calif. (catalog numbers 555427; 555428; 555426)]; and 24C02 [Lab Vision Corporation, Freemont, Calif. (catalog number MS-1279); United States Biological, Swampscott, Mass.].

Those skilled in the art will recognize that the designations $SC20^+$ and $CD24^+$ as well as $SC20^{-/lo}$ and $CD24^{-/lo}$ are synonymous and are used interchangeably throughout this application. CNS-SC isolated from fetal brains are $CD133^+$ $SC20^{-/lo}$ cells (e.g. the cells express low levels of CD24). When CNS-SC are expanded in vitro as neurosphere cells, they may express CD24. The CD24 antigen appears to be upregulated as cells proliferate. Therefore, neurosphere cells derived from CNS-SC are heterogeneous for CD24 express (low levels to high). Such cells are also $CD133^+$.

CD49f (also known as integrin alpha-6) (GenBank Accession No. X53586; SWISSPROT Accession No. P23229) is a 150 kDa transmembrane protein that is part of an integrin heterodimer expressed predominantly by epithelial cells. Integrin alpha-6 associates with the integrin β-1 (CD29) chain to form VLAA-6 and with the integrin β-4 chain to form the laminin and kalinin receptors. CD49f is expressed mainly on T cells, monocytes, platelets, epithelial and endothelial cells, perineural cells, and trophoblasts of placenta. The sequence of CD49f may be found in, e.g., Tamura et al., J. Cell Biol. 111:1593-604 (1990), which is incorporated herein by reference. There are two alternatively spliced forms of CD49f cDNA, which have been described as having different cytoplasmic domains. The A form alone is expressed in the lung, liver, spleen, and cervix. Only the B form is observed in the brain, ovary, and kidney, and both forms have been detected in other tissues. CD49f/CD29 α6β1 is the laminin receptor on platelets, monocytes, and T lymphocytes, and CD49f/CD29-mediated T cell binding to laminin provides a co-stimulatory signal to T cells for activation and proliferation.

Antibodies to CD49f have not been used in methods for identifying, isolating, or enriching for non-hematopoietic stem cells or progenitor cells, particularly central nervous system (CNS) neural stem cells and progenitor cells.

The sequence of CD49f is presented below in Table A. Alpha-6 associates with the integrin β-1 (CD29) chain to form VLAA-6 and with the integrin β-4 claim to form the laminin and kalinin receptors. Antibodies that recognize CD49f include GoH3 [Research Diagnostics, Inc., Flanders, N.J. (catalog numbers RDI-M1566 and RDI-M1672clb); BD Biosciences (www.bdbiosciences.com) (catalog numbers 55710, 557511, 551140, 551129, 555734, 555735, 555736); and ICN Biomed (www.incbiomed.com)] and 4F10 [Research Diagnostics, Inc., Flanders, N.J. (catalog number RDI-CBL458)].

Antibodies that recognize human CD15 include MMA (BD Biosciences (www.bdbiosciences.com) (catalog numbers 340703, 340850, 347420, 347423, 559045)).

Cell surface carbohydrate moieties are useful cell type markers (Jessell et al., (1990) Ann. Rev. Neurosci 13, 227-55). The LeX antigen, which is the trisaccharide 3-fucosyl-N-acetyllactosamine or FAL (Gooi et al., (1981) Nature 292, 156-58), also known as SSEA-1 (stage specific

TABLE A

SEQUENCE OF CD49f (SEQ ID NO:1)

| | | | | | | |
|---|---|---|---|---|---|---|
| 1 | maaagqlcll | ylsagllsrl | gaafnldtre | dnvirkygdp | gslfgfslam | hwqlqpedkr |
| 61 | lllvgaprge | alplqranrt | gglyscdita | rgpctriefd | ndadptsesk | edqwmgvtvq |
| 121 | sqgpggkvvt | cahryekrqh | vntkqesrdi | fgrcyvlsqn | lrieddmdgg | dwsfcdgrlr |
| 181 | ghekfgscqq | gvaatftkdf | hyivfgapgt | ynwkgivrve | qknntffdmn | ifedgpyevg |
| 241 | getehdeslv | pvpansylgl | lfltsvsytd | pdqfvyktrp | preqpdtfpd | vmmnsylgfs |
| 301 | ldsgkgivsk | deitfvsgap | ranhsgavvl | lkrdmksahl | lpehifdgeg | lassfgydva |
| 361 | vvdlnkdgwq | divigapqyf | drdgevggav | yvymnqqgrw | nnvkpirlng | tkdsmfgiav |
| 421 | knigdinqdg | ypdiavgapy | ddlgkvfiyh | gsangintkp | tqvlkgispy | fgysiagnmd |
| 481 | ldrnsypdva | vgslsdsvti | frsrpviniq | ktitvtpnri | dlrqktacga | psgiclqvks |
| 541 | cfeytanpag | ynpsisivgt | leaekerrks | glssrvqfrn | qgsepkytqe | ltlkrqkqkv |
| 601 | cmeetlwlqd | nirdklrpip | itasveiqep | ssrrrvnslp | evlpilnsde | pktahidvhf |
| 661 | lkegcgddnv | cnsnlkleyk | fctregnqdk | fsylpiqkgv | pelvlkdqkd | ialeitvtns |
| 721 | psnprnptkd | gddaheakli | atfpdtltys | ayrelrafpe | kqlscvanqn | gsqadcelgn |
| 781 | pfkrnsnvtf | ylvlsttevt | fdtpdldinl | klettsnqdn | lapitakakv | vielllsvsg |
| 841 | vakpsqvyfg | gtvvgeqamk | sedevgslie | yefrvinlgk | pltnlgtatl | niqwpkeisn |
| 901 | gkwllylvkv | eskglekvtc | epqkeinsln | lteshnsrkk | reitekqidd | nrkfslfaer |
| 961 | kyqtlncsvn | vncvnircpl | rgldskasli | lrsrlwnstf | leeysklnyl | dilmrafidv |
| 1021 | taaaenirlp | nagtqvrvtv | fpsktvaqys | gvpwwiilva | ilagilmlal | lvfilwkcgf |
| 1081 | fkrsryddsv | pryhavrirk | eereikdeky | idnlekkqwi | tkwnrnesys | |

CD15 (also known as Lewis X, or LeX) (GenBank Accession No. NM 002033) is a 220 kDa branched pentasaccharide. The CD15 carbohydrate epitope is expressed in mature human neutrophils, monocytes, and eosinophils, as well as in adult mouse subventricular zone (SVZ) stem cells. It can also be found present on embryonic tissues and adenocarcinomas, myeloid leukemias and Reed-Sternberg cells. In such tissues, the Lewis X epitope is considered to be involved in cell-cell interactions. CD15 is carried by the CD11/CD18 and CD66 glycoproteins. CD15 antibodies recognize the terminal trisaccharide structure Galβ1→4 [Fucα1→3]GlcNAc (LeX antigen). The majority of the CD15 antibodies are IgM, and they do not cross react with form of CD15, CD15s.

CD15 is a fucose-containing trisaccharide widely distributed in many tissues and is developmentally expressed in some rodent and human tissues, i.e., brain and lung, and mouse early embryo. Additionally, CD15 is present on the surface of pluripotent stem cells, such as mouse embryonic stem cells and primordial germ cells. The sequence of CD15 is presented in Table B. CD15 is useful as a cell type marker since it allows for stem cell localization and purification.

embryonic antigen 1) or CD15 (leukocyte cluster of differentiation 15), is highly expressed on pluripotent stem cells: it is found on mouse and human embryonic carcinoma cells, mouse pre-implantation embryos, embryonic stem cells, teratocarcinoma cells and primordial germ cells (Solter and Knowles, (1978) Proc. Natl. Acad. Sci. USA 75, 5565-69; Fox et al., (1981) Dev. Biol. 83, 391-98; Bird and Kimber, (1984) Dev. Biol. 104, 449-60; Muramatsu, (1994) Nagoya J. Med. Sci. 57, 95-108; Marani et al., (1986) Acta. Morphol. Neerl. Scand. 24, 103-110; Gomperts et al., (1994) Development 120, 135-41). Intriguingly, CNS cell sub-populations in various species also express this marker during development and in adulthood. LeX is expressed in germinal zones in the murine embryonic telencephalon (Yamamoto et al., (1985) Proc. Natl. Acad. Sci. USA 82, 3045-49; Allendoerfer et al., (1995) Mol. Cell. Neurosci. 6, 381-95; Allendoerfer et al., (1999) Dev. Biol. 211, 208-19; Tole et al., (1995) J. Neurosci 15, 624-27; Ashwell and Mai, (1997) Cell Tissue Res. 289, 17-23) and spinal cord (Dodd and Jessell, (1986) J. Exp. Biol. 129, 225-38), and in the cerebellar external granular layer (Marani and Tetteroo, (1983) Histochemistry 78, 157-61. In the adult mouse CNS, LeX is expressed by sub-populations of astrocytes, tanycytes, and a few neurons (Bartsch and Mai, (1991) Cell Tissue Res. 263, 353-66; Gocht et al., (1996) Histol. Histopathol. 11, 1007-28; Ashwell and Mai, (1997) Cell Tissue Res. 289, 17-23).

TABLE B

SEQUENCE OF CD15 (SEQ ID NO:2)

```
   1 ctgctcctgc gcggcagctg ctttagaagg tctcgagcct cctgtacctt cccagggatg
  61 aaccgggcct tccctctgga aggcgagggt tcgggccaca gtgagcgagg gccagggcgg
 121 tgggcgcgcg cagagggaaa ccggatcagt tgagagagaa tcaagagtag cggatgaggc
 181 gcttgtgggg cgcggcccgg aagccctcgg gcgcgggctg ggagaaggag tgggcggagg
 241 cgccgcagga ggctcccggg gcctggtcgg gccggctggg ccccgggcgc agtggaagaa
 301 agggacgggc ggtgcccggt tgggcgtcct ggccagctca ccttgccctg gcggctcgcc
 361 ccgccgcca cttgggagga gcagggcagg gcccgcggcc tttgcattct gggaccgccc
 421 ccttccattc ccgggccagc ggcgagcggc agcgacggct ggagccgcag ctacagcatg
 481 agagccggtg ccgctcctcc acgcctgcgg acgcgtggcg agcggaggca gcgctgcctg
 541 ttcgcgccat gggggcaccg tggggctcgc cgacggcggc ggcgggcggg cggcgcgggt
 601 ggcgccgagg ccggggctg ccatggaccg tctgtgtgct ggcggccgcc ggcttgacgt
 661 gtacggcgct gatcacctac gcttgctggg ggcagctgcc gccgctgccc tgggcgtcgc
 721 caaccccgtc gcgaccggtg ggcgtgctgc tgtggtggga gccctttcggg gggcgcgata
 781 gcgccccgag gccgcccct gactgccggc tgcgcttcaa catcagcggc tgccgcctgc
 841 tcaccgaccg cgcgtcctac ggagaggctc aggccgtgct ttttccaccac cgcgacctcg
 901 tgaaggggcc ccccgactgg ccccgccct ggggcatcca ggcgcacact gccgaggagg
 961 tggatctgcg cgtgttggac tacgaggagg cagcggcggc ggcagaagcc ctggcgacct
1021 ccagcccccag gccccccggc cagcgctggg tttggatgaa cttcgagtcg ccctcgcact
1081 ccccgggggct gcgaagcctg gcaagtaacc tcttcaactg gacgctctcc tacgggcgg
1141 actcggacgt ctttgtgcct tatggctacc tctacccag aagccacccc ggcgacccgc
1201 cctcaggcct ggccccgcca ctgtccagga aacaggggct ggtggcatgg gtggtgagcc
1261 actgggacga gcgccaggcc cgggtccgct actaccacca actgagccaa catgtgaccg
1321 tggacgtgtt cggccggggc gggccggggc agccggtgcc cgaaattggg ctcctgcaca
1381 cagtggcccg ctacaagttc tacctggctt tcgagaactc gcagcacctg gattatatca
1441 ccgagaagct ctggcgcaac gcgttgctcg ctggggcggt gccggtggtg ctgggcccag
1501 accgtgccaa ctacgagcgc tttgtgcccc gcggcgcctt catccacgtg gacgacttcc
1561 caagtgcctc ctccctggcc tcgtacctgc ttttcctcga ccgcaacccc gcggtctatc
1621 gccgctactt ccactggcgc cggagctacg ctgtccacat cacctccttc tgggacgagc
1681 cttggtgccg ggtgtgccag gctgtacaga gggctgggga ccggcccaag agcatacgga
1741 acttggccag ctggttcgag ccggtgaagcc gcgctcccct ggaagcgacc caggggaggc
1801 caagttgtca gcttttgat cctctactgt gcatctcctt gactgccgca tcatgggagt
1861 aagttcttca aacacccatt tttgctctat gggaaaaaaa cgatttacca attaatatta
1921 ctcagcacag agatggggc ccggtttcca tattttttgc acagctagca attgggctcc
1981 ctttgctgct gatgggcatc attgtttagg ggtgaaggag ggggttcttc ctcaccttgt
2041 aaccagtgca gaaatgaaat agcttagcgg caagaagccg ttgaggcggt ttcctgaatt
2101 tccccatctg ccacaggcca tatttgtggc ccgtgcagct tccaaatctc atacacaact
2161 gttcccgatt cacgttttc tggaccaagg tgaagcaaat ttgtggttgt agaaggagcc
```

TABLE B-continued

SEQUENCE OF CD15 (SEQ ID NO:2)

```
2221 ttgttggtgg  agagtggaag  gactgtggct  gcaggtggga  ctttgttgtt  tggattcctc
2281 acagccttgg  ctcctgagaa  aggtgaggag  ggcagtccaa  gaggggccgc  tgacttcttt
2341 cacaagtact  atctgttccc  ctgtcctgtg  aatggaagca  aagtgctgga  ttgtccttgg
2401 aggaaactta  agatgaatac  atgcgtgtac  ctcactttac  ataagaaatg  tattcctgaa
2461 aagctgcatt  taaatcaagt  cccaaattca  ttgacttagg  ggagttcagt  atttaatgaa
2521 accctatgga  gaatttatcc  ctttacaatg  tgaatagtca  tctcctaatt  tgtttcttct
2581 gtctttatgt  ttttctataa  cctggatttt  ttaaatcata  ttaaaattac  agatgtgaaa
2641 ataagcaga   agcaaccttt  ttccctcttc  ccagaaaacc  agtctgtgtt  tacagacaga
2701 agagaaggaa  gccatagtgt  cacttccaca  caattattta  tttcatgtct  ttactggacc
2761 tgaaatttaa  actgcaatgc  cagtcctgca  ggagtgctgg  cattaccctc  tgcagaacag
2821 tgaaaggtat  tgcactacat  tatggaatca  tgcaaaaaaa  a
```

At least two different subsets of CD133+SC20$^{-/lo}$ cells exist: those that are CD15$^{-/lo}$ and those that are CD15$^{hi}$. Both subsets expanded to give rise to neurospheres. It is unclear whether CD15$^{-/lo}$ or CD15$^{hi}$ cells are more primitive CNS-SC. Neurosphere cells derived from the CD15$^{-/lo}$ subset of cells engrafted well in the NOD-SCID mouse.

Biological Significance of CD15 (LeX)

LeX is expressed on embryonic pluripotent stem cells and on adult CNS stem cells. LeX influences blastocyst adhesion, (Bird, J. M. et al., (1984) Dev. Biol. 104, 449-460; Hakomori, S. I. (1992) Histochem. J. 24, 771-776), and it can influence CNS stem cell adhesion. Carbohydrate ectodomains on proteoglycans can be shed into the extracellular matrix where they interact with growth factors (Kato, M. et al., (1998) Nat. Med. 4, 691-697). LeX is present in the extracellular matrix (Gocht, A. et al., (1996) Histol. Histopathol. 11, 1007-1028) and shedding of LeX+ material by adult SVZ cells in vitro and diffuse LeX staining in neurogenic zones has been observed. Low concentrations of free LeX can promote FGF2 oligomerization and stimulate its mitogenicity for embryonic stem cells (Milev, P. et al., (1998) J. Biol. Chem. 273, 21439-21442; Jirmanova, L. et al., (1999) Int. J. Dev. Biol. 43, 555-562). However, excess LeX inhibits FGF2 mitogenicity (Dvorak, P. et al., (1998) J. Cell Science 111, 2945-2952). Thus, different concentrations of LeX in the extracellular environment can regulate growth factor access to, and influence on, CNS stem cells. In the embryo, LeX-containing carbohydrates can bind Wnts, and they may continue to bind critical growth modulators in the adult. The large carrier molecule for LeX identified in the developing CNS and adult neurogenic regions may be important to its regulative role.

Isolation of Subsets of Stem and Progenitor Cells

Establishing a hierarchy of a particular cell fate map has now been accomplished for the mouse hematopoietic stem cells and its progeny. This fate mapping uses the techniques that have been applied in this invention and can be found more descriptively in Morrison S J, Weissman I L. Immunity 1994 Nov;1(8):661-73; Kondo M, Weissman I L, Akashi K. Cell 1997 Nov 28;91(5):661-72; Akashi K, Traver D, Miyamoto T, Weissman I L. Nature 2000 Mar 9;404(6774):193-7. The further dissection of the initially described mouse hematopoietic stem cell population was accomplished by using surface phenotypes to subdivide the hematopoietic stem cell population into both a short and long term repopulating fraction. This technology was then applied to the progeny of the hematopoietic stem cells to identify a lymphomyeloid progenitor; a myeloid restricted progenitor, and a common lymphoid progenitor.

Isolation of Subsets of NS-IC

NS-IC are obtained from a cell population isolated from neural tissues (typically fetal brain tissue), prior to expansion in vitro. As a result, the NS-IC population can be CD133+CD24$^{-/lo}$ or CD49f+CD24$^{-/lo}$. Following in vitro expansion, this population of cells may be CD24$^{hi}$. NS-IC obtained following culture can be classified as CD133+ CD49f+.

The invention provides for selection methodologies using the cellular marker CD49f that can be used to isolate subsets of NS-IC (including stem cells and progenitors). Isolation of such subsets can be performed either before or after selection of CD133+ cells and/or CD49f+ cells. CD15 can be used to isolate CD15$^{hi}$CD24$^{-/lo}$ and CD133+CD15$^{-/lo}$CD24$^{-/lo}$ cell populations, which are enriched for NS-IC. As shown in FIG. 7, CD15 expression defines different subsets of expandable CNS stem cells and progenitors. As shown in Example 6, CD15$^{-/lo}$ cells have the ability to generate neurospheres and engraft well following transplantation.

Cell Deposits The 8G1.7 culture (now known as SC20) has been deposited on Dec. 20, 1999 with ATCC, 10801 University Blvd., Manassas, Va. 20110-2209, under ATCC accession number PTA-993 in accordance with the provisions of the Budapest Treaty for the Deposit of Microorganisms. In accordance with the provisions of the Budapest Treaty, all restrictions on the availability to the public of the deposited material will be irrevocably removed upon the granting of a patent. As noted in U.S. Pat. No. 5,843,633, the murine hybridoma cell line AC133 was deposited at the American Type Tissue Collection, 12301 Parklawn Drive, Rockville, Md. 20852 (ATCC designation HB12346) in accordance with the provisions of the Budapest Treaty.

Anti-CD49f and anti-CD15 antibodies are commercially available.

Isolation, enrichment, and selection of cells. The population of cells from which NS-ICs are isolated can be a neural tissue, a population of cells dissociated from neural tissue, or a population of cells in cell culture, e.g., cells in a neurosphere culture or an adherent neural stem cell culture.

The invention provides for the isolation and identification of NS-ICs. Identification of a neurosphere initiating stem cell or progenitor (NS-IC) involves contacting a population of neural cells (or a population which contains neural or neural derived cells) with a reagent that binds to the CD49f antigen and/or a reagent that binds to the CD133 antigen and/or a reagent that binds to the CD15 antigen, and detecting the contact between the reagent that binds to the CD49f and/or CD133 and/or CD15 antigens and the CD49f and/or CD133 and/or CD15 antigens on the surface of cells. Those cells to which the CD49f and/or CD133 and/or CD15 reagents (e.g. CD15$^{hi}$ or CD15$^{-/lo}$ cells) bind are identified as NS-ICs. The identity of these cells can be confirmed by assays that demonstrate that the cells are in fact NS-ICs, capable of neurosphere initiation, self-renewal and multipotency.

The methods of this invention can also be used to isolate CD49f$^+$ cells from CD49f cells using an anti-CD49f antibody (or CD15$^{hi}$ cells or CD133$^+$CD15$^{-/lo}$CD24$^{-/lo}$ cells using an anti-CD15 antibody), by combining a population of neural cells which contains a fraction of NS-ICs with a reagent that specifically binds to the CD49f antigen (or the CD15 antigen), and then selecting for CD49f$^+$ cells (or for CD15$^{hi}$ or CD15$^{-/lo}$ cells), to produce a selected population enriched in CD49f$^+$ NS-ICs (or to the CD15$^{hi}$ or CD133$^+$ CD15$^{-/lo}$CD24$^{-/lo}$ NS-ICs) as compared with the population of neural cells prior to the selection. Accordingly, the invention further provides for the enrichment of NS-ICs from neural tissue or neural stem cell cultures (e.g., neurosphere suspension cultures or neural stem cell adherent cultures). The invention is thus useful for the enrichment of NS-IC from neural tissue in which stem cells and progenitor cells occur at low frequency, or may have been depleted, such as late embryo, juvenile, and/or adult tissue. One of ordinary skill in the art can combine a population of neural cells containing a fraction of NS-ICs with a reagent that specifically binds to the CD49f antigen or the to CD15 antigen, and select for the CD49f$^+$, CD15$^+$, or CD133$^+$ CD15$^{-/lo}$CD24$^{31/lo}$ cells. In this way, the selected CD49f$^+$, CD15$^+$, or CD133$^+$CD15$^{-/lo}$CD24$^{-/lo}$ cells are enriched in the fraction of NS-IC as compared with the population of neural cells.

The invention also provides antibodies that specifically binds to the CD49f antigen, wherein the CD49f antigen specifically binds to the GoH3 and/or 4F10 antibodies. This antibody may be produced by a hybridoma cell line. This monoclonal antibody may block simultaneous binding to the CD49f antigen by the antibody GoH3 and/or the antibody 4F10. Of particular interest are antibodies that bind to the CD49f antigen, cross-reactive antibodies (i.e., those which bind to the same epitope as the GoH3 and/or 4F10 antibodies and substantially inhibit simultaneous binding), species analogs thereof, binding fragments thereof, and/or conjugates thereof.

Likewise, the invention also provides antibodies that specifically binds to the CD15 antigen, wherein the CD15 antigen specifically binds to the MMA antibody. This antibody may be produced by a hybridoma cell line. This monoclonal antibody may block simultaneous binding to the CD15 antigen by the antibody MMA. Of particular interest are antibodies that bind to the CD15 antigen, cross-reactive antibodies (i.e., those which bind to the same epitope as the MMA antibody and substantially inhibit simultaneous binding), species analogs thereof, binding fragments thereof, and/or conjugates thereof.

Also provided is a method for the further enrichment of human CNS-SC and progenitors which can initiate neurospheres (NS-IC) by combining a population of CD49f$^+$ or a population of CD15$^+$ or CD15$^{-/lo}$ neural or neural-derived cells with a reagent that specifically binds to the CD24 antigen and removing those cells that are CD24$^+$, wherein the remaining cells are enriched for NS-IC. For example, this reagent can be an antibody.

In any of the methods of this invention, the population of neural or neural-derived cells can be further enriched by contacting the cells with a reagent that specifically binds to the CD133 antigen (i.e., an anti-CD133 antibody such as the AC133 monoclonal antibody) before, during, and/or after contacting the cells with a reagent that binds to the CD49f antigen. Likewise, in any of the methods of this invention, the population of neural or neural-derived cells can be further enriched by contacting the cells with a reagent that specifically binds to the CD15 antigen (i.e., an anti-CD15 antibody) before, during, and/or after contacting the cells with a reagent that binds to the CD49f antigen.

Cell selection according to the invention can be accomplished by any suitable means known in the art, including flow cytometry, such as by fluorescence activated cell sorting using fluorochrome conjugated antibodies. The selection can also be by high gradient magnetic selection using antibodies conjugated to magnetic particles. Likewise, any other suitable method including attachment to and disattachment from solid phase, is also contemplated as being within the scope of the invention.

A population of cells can be derived by immunoselection using an anti-CD49f antibody. The population of cells should contain at least 30% CD49f$^+$ NS-ICs, preferably at least 50-70% CD49f$^+$ NS-ICs, and more preferably greater than 90% CD49f$^+$ NS-ICs. Most preferable would be a substantially pure population of CD49f$^+$ NS-ICs, containing at least 95% CD49f$^+$ NS-ICs. The degree of enrichment obtained, and actually used, depends on a number of factors, including the method of selection, the method of growth, and the cell dose of the cells that are placed in culture for the initiation of neurospheres.

The population of cells can be derived from late embryo, juvenile, or adult mammalian CNS tissue, or it may be derived from existing cultures of neural stem cells, as described in Weiss, U.S. Pat. No. 5,750,376, or Johe, U.S. Pat. No. 5,753,506. In the most preferred embodiment, the NS-IC are human. In some embodiments, the CD49f$^+$ cells in the population can be complexed to endothelial cells.

The in vitro cell cultures described herein containing an enriched population of CD49f$^+$ NS-ICs are generally characterized as staining positive for nestin and, in the presence of differentiation-inducing conditions, produce progeny cells that differentiate into neurons, astrocytes, and oligodendrocytes.

One skilled in the art can introduce an isolated CD49f$^+$ cell to a culture medium, proliferate the isolated CD49f$^+$ cell in culture, particularly as a neurosphere; culture the progeny of the isolated CD49f$^+$ cell under conditions in which the isolated CD49f$^+$ cell differentiates to neurons, astrocytes, and oligodendrocytes; then detect the presence of neurons, astrocytes, and oligodendrocytes. The presence of neurons, astrocytes, and oligodendrocytes characterizes the isolated CD49f$^+$ cell as an NS-IC.

Typically, CD49f+ NS-ICs are cultured in a medium that permits the growth and proliferation of neurospheres. The culture in which the isolated CD49f+ cell proliferates can be a serum-free medium containing one or more predetermined growth factors effective for inducing multipotent neural stem cell proliferation. The culture medium can be supplemented with a growth factor selected from leukemia inhibitory factor (LIF), epidermal growth factor (EGF), basic fibroblast growth factor (FGF-2; bFGF) or combinations thereof. The culture medium can be further supplemented with neural survival factor (NSF) (Clonetics, Calif.). The conditions in which the CD49f+ cell differentiates to neurons, astrocytes, and oligodendrocytes can include culturing the CD49f+ cell progeny on a laminin-coated surface in culture medium containing fetal bovine serum (FBS) without EGF, FGF-2 or LIF.

The invention also provides a method for identifying the presence of a growth factor that affects the growth of NS-IC. One skilled in the art can combine a composition suspected of containing at least one growth factor that affects the growth of NS-IC with a composition containing NS-IC, then determine the growth of the NS-IC as a function of the presence of the composition. Altered (increased, decreased, etc.) NS-IC growth indicates the presence in the composition of a growth factor that affects the growth of NS-IC. The identity of the growth factor can be determined using techniques known in the art.

Antibodies to CD133. Antibodies to CD133 may be obtained or prepared as discussed in U.S. Pat. No. 5,843,633, incorporated herein by reference. The CD133 antigen can be contacted with an antibody, such as various anti-CD133 monoclonal antibodies (e.g., AC133), which have specificity for the CD133 antigen. "Anti-CD133 antibodies" are characterized by binding to the CD133 protein in native, in FACS, and immunoprecipitation experiments, as well as denatured, in Western blot experiments, conformations. The CD133 antigen has been reported to have molecular weights in the range of 125 kDa to 127 kDa according to U.S. Pat. No. 5,843,633 and 115 kDa to 127 kDa according to United States Published Patent Application No. 20010051372. The CD133 antigen is expressed on a subset of progenitor cells derived from human bone marrow, fetal bone marrow and liver, cord blood, and adult peripheral blood.

Antibodies to CD49f Antibodies to CD49f may be obtained commercially or prepared according to methods known to those of ordinary skill in the art. The CD49f antigen can be contacted with an antibody, such as various anti-CD49f monoclonal antibodies, which have specificity for the CD49f antigen. Anti-CD49f antibodies are characterized by binding to the CD49f antigen under Western blot conditions from reducing SDS-PAGE gels. As used herein, the term "anti-CD49f antibody" refers to a monoclonal or polyclonal antibody that specifically binds to the CD49f antigen. Examples of anti-CD49f antibodies include, but are not limited to, GoH3 and 4F10. The CD49f antigen has a molecular weight, based on commercially available standards, in the range of about 140 kDa. The CD49f antigen is expressed on thyrnocytes, T lymphocytes, and monocytes. Increased expression is found on activated and memory T cells. The A splice variant alone is expressed in the lung, liver, spleen and cervix. The B splice variant alone is expressed in the brain, ovary, and kidney. Both forms are also detected in other tissues.

Antibodies to CD15. Antibodies to human CD15 may be obtained commercially or prepared according to methods known to those of ordinary skill in the art. The CD15 antigen can be contacted with an antibody, such as various anti-CD15 monoclonal antibodies, which have specificity for the CD15 antigen. Anti-CD15 antibodies are characterized by binding to the CD15 antigen under Western blot conditions from reducing SDS-PAGE gels. As used herein, the term "anti-CD15 antibody" refers to a monoclonal or polyclonal antibody that specifically binds to the CD15 antigen. Examples of anti-CD15 antibodies include, but are not limited to, MMA. The CD15 antigen has a molecular weight, based on commercially available standards, in the range of about 220 kDa. The CD15 antigen is expressed in mature human neutrophils, monocytes, and eosinophils. It can also be found present on embryonic tissues and adenocarcinomas, myeloid leukemias and Reed-Stemberg cells.

Preparation of antibodies. Antibodies to the CD133, CD49f and/or CD15 antigens can be obtained by immunizing a xenogeneic immunocompetent mammalian host (including murine, rodentia, lagomorpha, ovine, porcine, bovine, etc.) with human progenitor cells. The choice of a particular host is primarily one of convenience. A suitable progenitor cell population for immunization can be obtained by isolating CD34+ cells from cytokine mobilized peripheral blood, bone marrow, fetal liver, etc. In addition, a suitable progenitor cell population for immunization can be obtained from CNS neural stem cells or other NS-IC. Immunizations are performed in accordance with conventional techniques, where the cells may be injected subcutaneously, intramuscularly, intraperitoneally, intravascularly, etc. Normally, from about $10^6$ to $10^8$ cells are used, which may be divided into one or more injections, usually not more than about 8 injections, over a period of from about one to about three weeks. The injections may be with or without adjuvant, e.g. complete or incomplete Freund's adjuvant, specol, alum, etc.

After completion of the immunization schedule, the antiserum may be harvested in accordance with conventional methods to provide polygonal antisera specific for the surface membrane proteins of progenitor cells, including the CD133, CD49f and/or CD15 antigens. Lymphocytes are harvested from the appropriate lymphoid tissue, e.g. spleen, draining lymph node, etc., and fused with an appropriate fusion partner, usually a myeloma line, producing a hybridoma secreting a specific monoclonal antibody. Screening clones of hybridomas for the antigenic specificity of interest is performed in accordance with conventional methods.

The anti-CD133, anti-CD49f and/or anti-CD15 antibodies can be produced as a single chain, instead of the normal multimeric structure. Single chain antibodies are described in e.g., Jost et al., 269 J. BIOL. CHEM. 26267-73 (1994), incorporated herein by reference. DNA sequences encoding the variable region of the heavy chain and the variable region of the light chain are ligated to a spacer encoding at least about 4 amino acids of small neutral amino acids, including glycine or serine. The protein encoded by this fusion allows assembly of a functional variable region that retains the specificity and affinity of the original antibody. Anti-CD133, anti-C49f and/or anti-CD15 antibodies can also be produced by use of Ig cDNA for construction of chimeric immunoglobulin genes (Liu et al., 84 PROC. NATL. ACAD. SCI. 3439 (1987) and 139 J. IMMUNOL. 3521 (1987), incorporated herein by reference. mRNA is isolated from a hybridoma or other cell producing the antibody and used to produce cDNA. The cDNA of interest may be amplified by the polymerase chain reaction using specific primers (U.S. Pat. No. 4,683,195 and U.S. Pat. No. 4,683,202).

Alternatively, a library is made and screened to isolate the sequence of interest. The DNA sequence encoding the variable region of the antibody is then fused to human constant region sequences. The sequences of human constant regions genes may be found in Kabat et al., "Sequences of Proteins of Immunological Interest" N.I.H. PUBLICATION No. 91-3242 (1991). Human C region genes are readily available from known clones. The chimeric, humanized antibody is then expressed by conventional methods.

Anti-CD133, anti-CD49f and/or anti-CD15 antibodies can also be produced as antibody fragments, such as Fv, F(ab')$_2$ and Fab. Antibody fragments may be prepared by cleavage of the intact protein, e.g. by protease or chemical cleavage. Alternatively, a truncated gene can be designed. For example, a chimeric gene encoding a portion of the F(ab')$_2$ fragment would include DNA sequences encoding the CH1 domain and hinge region of the H chain, followed by a translational stop codon to yield the truncated molecule.

Immunostaining. Biological samples are assayed for the presence of CD133$^+$, CD49f$^+$ and/or CD15$^+$ or CD15$^{-/lo}$ cells by any convenient immunoassay method for the presence of cells expressing the surface molecule bound by the subject antibodies. Assays may be performed on cell lysates, intact cells, frozen sections, etc. Any commercially available antibodies are suitable for the direct immunofluorescent staining of cells.

Cell sorting. The use of cell surface antigens found on NS-IC cells provides a means for the positive immunoselection of progenitor cell populations, as well as for the phenotypic analysis of progenitor cell populations using flow cytometry. Cells selected for expression of CD49f and/or CD15 antigen may be further purified by selection for other stem cell and progenitor cell markers, including CD133.

For the preparation of substantially pure progenitors and stem cells, a subset of progenitor cells is separated from other cells on the basis of CD49f and/or CD15 binding. Progenitors and stem cells may be further separated by binding to other surface markers known in the art, including CD133. Selection of CD133$^+$ cells may be accomplished before, during or after selection of CD49f$^+$ and/or CD15$^+$ or CD15$^{-/lo}$ cells. Likewise, selection of CD15$^+$ or CD15$^{-/lo}$ cells may be accomplished before, during or after selection of CD49f$^+$ and/or CD133$^+$ cells. Procedures for separation may include magnetic separation, using antibody-coated magnetic beads, affinity chromatography and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. Dead cells may be eliminated by selection with dyes associated with dead cells (propidium iodide [PI], LDS). Any technique, which is not unduly detrimental to the viability of the selected cells, known to those in the art may be employed.

Conveniently, the antibodies are conjugated with labels to allow for ease of separation of the particular cell type, e.g. magnetic beads; biotin, which binds with high affinity to avidin or streptavidin; fluorochromes, which can be used with a fluorescence activated cell sorter; haptens; and the like. Multi-color analyses may be employed with the FACS or in a combination of immunomagnetic separation and flow cytometry. Multi-color analysis is of interest for the separation of cells based on multiple surface antigens, e.g. CD49$^+$CD24$^{-/lo}$, CD49fCD24$^+$, CD15$^+$CD24$^{-/lo}$, CD15$^{-/lo}$CD24$^+$, CD15$^{-/lo}$CD24$^{-/lo}$, CD133$^+$CD49f$^+$CD24$^{-/lo}$, CD133$^-$CD49f$^-$CD24$^+$, CD133$^+$CD15$^+$CD24$^{-/lo}$, CD133$^-$CD15$^{-/lo}$CD24$^+$, CD133$^+$CD15$^{-/lo}$CD24$^{-/lo}$, CD133$^+$CD49$^+$CD15$^+$CD24$^{-/lo}$, CD133$^-$CD49fCD15$^{-/lo}$CD24$^+$, CD133$^+$CD49f$^+$CD15$^{-/lo}$CD24$^{-/lo}$, etc.

Fluorochromes, which find use in a multi-color analysis include phycobiliproteins, e.g. phycoerythrin and allophycocyanins; fluorescein and Texas red. A negative designation indicates that the level of staining is at or below the brightness of an isotype matched negative control. A dim or low designation indicates that the level of staining may be near the level of a negative stain, but may also be brighter than an isotype matched control.

In one embodiment, the anti-CD133, anti-CD49f and/or anti-CD15 antibodies are directly or indirectly conjugated to a magnetic reagent, such as a superparamagnetic microparticle (microparticle). Direct conjugation to a microparticle can be achieved by use of various chemical linking groups, as known in the art. The antibody can be coupled to the microparticles through side chain amino or sulfhydryl groups and heterofunctional cross-linking reagents. A large number of heterofunctional compounds are available for linking to entities. A preferred linking group is 3-(2-pyridyidithio)propionic acid N-hydroxysuccinimide ester (SPDP) or 4-(N-maleimidomethyl)-cyclohexane-1-carboxylic acid N-hydroxysuccinimide ester (SMCC) with a reactive sulfhydryl group on the antibody and a reactive amino group on the magnetic particle.

Alternatively, the anti-CD133, anti-CD49f and/or anti-CD15 antibodies can be indirectly coupled to the magnetic particles. The antibody is directly conjugated to a hapten, and hapten-specific, second stage antibodies are conjugated to the particles. Suitable haptens include digoxin, digoxigenin, FITC, dinitrophenyl, nitrophenyl, avidin, biotin, etc. Methods for conjugation of the hapten to a protein are known in the art, and kits for such conjugations are commercially available.

To practice the methods of the invention, the anti-CD49f and/or anti-CD15 antibodies are added to a cell sample. The amount of anti-CD49f and/or anti-CD15 antibody necessary to bind a particular cell subset is empirically determined by performing a test separation and analysis. The cells and anti-CD49f and/or anti-CD15 antibodies are incubated for a period of time sufficient for complexes to form, usually at least about 5 minutes, more usually at least about 10 minutes, and usually not more than one hour, more usually not more than about 30 minutes.

The cells may additionally be incubated with antibodies or binding molecules specific for cell surface markers known to be present or absent on progenitor or stem cells. For example, the cells can be incubated with an anti-CD133 antibody either prior to, during, or after incubation with an anti-CD49f and/or anti-CD15 antibody to produce a further enriched population of NS-IC. The cells can be incubated with an anti-CD15 antibody either prior to, during, or after incubation with an anti-CD49f and/or anti-CD133 antibody to produce a further enriched population of NS-IC. The labeled cells are separated in accordance with the specific antibody preparation. Fluorochrome labeled antibodies are useful for FACS separation, magnetic particles for immunomagnetic selection, particularly high gradient magnetic selection (HGMS), etc. Exemplary magnetic separation devices are described in WO 90/07380, PCT/US96/00953, and EP 438,520, each of which is incorporated herein by reference. The AC133 Cell Isolation Kit (Miltenyi Biotec Inc., Auburn Calif.) can be used for the positive selection of AC133$^+$ cells. The kit provides a tool for single step isolation of AC133$^+$ cells (i.e., cells that have the CD133 antigen. The AC133 Cell Isolation Kit contains FcR Blocking Reagent and MACS colloidal MicroBeads conjugated to the monoclonal mouse anti-human AC133 antibody.

The purified cell population may be collected in any appropriate medium. Various commercially available media may be used, including Dulbecco's Modified Eagle Medium (DMEM), Hank's Basic Salt Solution (HBSS), Dulbecco's phosphate buffered saline (DPBS), RPMI, Iscove's modified Dulbecco's medium (IMDM), phosphate buffered saline (PBS) with 5 mM EDTA, etc., frequently supplemented with fetal calf serum (FCS), bovine serum albumin (BSA), human serum albumin (HSA), etc.

Populations highly enriched for human progenitor or stem cells are achieved in this manner. The desired cells will be 30% or more of the cell composition, preferably 50% or more of the cell population, more preferably 90% or more of the cell population, and most preferably 95% or more (e.g. substantially pure) of the cell population.

Use of purified stem cell/progenitor cells. $CD133^+$ $CD49f^+$, $CD133^+CD15^+$, $CD133^+CD15^{-/lo}$, $CD133^+$ $CD49f^+CD15^+$, $CD133^+CD49f^+CD15^{-/lo}$, $CD15^{-/lo}CD49f^+$, and/or $CD15^+CD49f^+$ stem cells/progenitor cells are useful in a variety of ways. The $CD133^+CD49f^+$, $CD133^+CD15^+$, $CD133^+CD15^{-/lo}$, $CD133^+CD49f^+CD15^+$, $CD133^+CD49f^+$ $CD15^{-/lo}$, $CD15^{-/lo}CD49f^+$, and/or $CD15^+CD49f^+$ cells can be used to reconstitute a host whose cells have been lost through disease or injury. Genetic diseases associated with cells may be treated by genetic modification of autologous or allogeneic stem cells to correct a genetic defect or treat to protect against disease. Alternatively, normal allogeneic progenitor cells may be transplanted. Diseases other than those associated with cells may also be treated, where the disease is related to the lack of a particular secreted product such as hormone, enzyme, growth factor, or the like. CNS disorders encompass numerous afflictions such as neurodegenerative diseases (e.g. Alzheimer's and Parkinson's), acute brain injury (e.g. stroke, head injury, cerebral palsy) and a large number of CNS dysfunctions (e.g. depression, epilepsy, and schizophrenia). In recent years neurodegenerative disease has become an important concern due to the expanding elderly population, which is at greatest risk for these disorders. These diseases, which include Alzheimer's Disease, Multiple Sclerosis (MS), Huntington's Disease, Amyotrophic Lateral Sclerosis, and Parkinson's Disease, have been linked to the degeneration of neural cells in particular locations of the CNS, leading to the inability of these cells or the brain region to carry out their intended function. By providing for maturation, proliferation and differentiation into one or more selected lineages through specific different growth factors the progenitor cells may be used as a source of committed cells. Neurospheres can also be used to produce a variety of blood cell types, including myeloid and lymphoid cells, as well as early hematopoietic cells (see, Bjornson et al., 283 SCIENCE 534 (1999), incorporated herein by reference).

The $CD133^+$ $CD49f^+$, $CD133^+CD15^+$, $CD133^+CD15^{-/lo}$, $CD133^+CD49f^+CD15^+$, $CD133^+CD49f^+CD15^{-/lo}$, $CD15^{-/lo}$ $CD49f^+$, and/or $CD15^+CD49f^+$ cells may also be used in the isolation and evaluation of factors associated with the differentiation and maturation of cells. Thus, the cells may be used in assays to determine the activity of media, such as conditioned media; to evaluate fluids for growth factor activity, involvement with dedication of lineages, or the like.

The $CD133^+$ $CD49f^+$, $CD133^+CD15^+$, $CD133^+CD15^{-/lo}$, $CD133^+CD49f^+CD15^+$, $CD133^+CD49f^+CD15^{-/lo}$, $CD15^{-/lo}$ $CD49f^+$, and/or $CD15^+CD49f^+$ cells may be frozen at liquid nitrogen temperatures and stored for long periods of time, being thawed and capable of being reused. The cells will usually be stored in 5% DMSO and 95% fetal calf serum. Once thawed, the cells may be expanded by use of growth factors or stromal cells associated with stem cell proliferation and differentiation.

The following examples are presented in order to more fully illustrate the preferred embodiments of the invention. These examples should in no way be construed as limiting the scope of the invention, as defined by the appended claims.

EXAMPLE 1

Isolation of NS-IC By Different Markers

The CD24 antigen, recognized by for example, the SC20 (8G1) monoclonal antibody, can also be evaluated as a subselector for neural stem cells. Cells that are $CD24^{-/lo}$ ($8G1^{-/lo}$) display more stem cell-like properties, while cells that are $CD24^{med/hi}$ ($8G1^{med/hi}$) display more progenitor cell-like properties (FIG. 3), in isolates of fresh fetal brain.

Following culture, CD24 expression can be upregulated depending on cell cycle status, days post last passage, and culture conditions. Thus, long-term neurosphere cells derived from $CD24^{-/lo}$ fetal brain cells become heterogeneous for CD24 expression.

EXAMPLE 2

Neurosphere Initiating Cells can be Separated Based on CD49f Expression: Flow Cytometry Cell Sorting (FACS) Approach The purpose of this EXAMPLE is to test whether $CD49f^+$ cells are the only cells in the brain that have pluripotent NSC activity. To measure neural stem cells and primitive progenitor activities, a NS-IC assay will be established to determine frequency of NS-IC in a given population. When NS-IC are rare and express CD49f antigen, NS-IC can be enriched by $CD49f^+$ selection, and correspondingly depleted in other fractions.

Source of monoclonal antibodies: CD49f antigen is recognized by at least the following monoclonal antibodies: GoH3 (Research Diagnostics, Inc. (Flanders, N.J.); BD Biosciences (www.bdbiosciences.com); and ICN Biomed (www.incbiomed.com)) and 4F10 (Research Diagnostics, Inc. (Flanders, N.J.)).

Human fetal brain (FBR 10-20 gestational week ["g.w"]) are obtained after obtaining informed consent. Human fetal brain tissues are cut into 1-3 mm cubed pieces using scalpels, transferred into 50 mL centrifuge tube and washed once with 0.02% EDTA/PBS solution. Tissue pieces are dissociated enzymatically in the presence of collagenase and hyaluronidase at 37 degrees or 1 hour.

During the next days, the dissociated tissue pieces are washed once with 0.02% EDTA/PBS solution and dissociated enzymatically in the presence of trypsin at 37 degrees for 15 minutes. Debris and aggregates are removed by filtering cell suspensions through 70 micron filter cup. Typically $1-10 \times 10^8$ cells were obtained from each FBr tissue, 16-20 gestational wk. Cells were resuspended in HBSS buffer containing 0.1% human serum albumin and 10 mM HEPES.

The staining and sorting of CNS-SC from FBr were performed as follows. Typically the dissociated FBr cells were incubated and stained with mAb against CD133, CD24-FITC, and CD49f-PE. Stained cells were washed and resuspended in HBSS containing 0.1% human serum albumin, 10 mM HEPES (Gibco) and 0.5 µg/mL of propidium iodine (PI) and sorted with a dual-laser Vantage SE (BDIS).

CD49f$^+$ CD24$^{-/lo}$ FACS separated cells are cultured in typically, X vivo 15 or combination of X vivo 15, D-MEM,/F-12 media is used as a basal media. To maximize neurosphere development, the sorted cells are typically cultured in the presence of LIF, FGF-2, EGF, as described in Example 3, infra. Neurosphere cells established from CD49F$^+$ CD24$^{-/lo}$ sorted cells will express nestin, as can be tested after approximately 7 days in culture and can be detected mouse anti-human nestin antibody (Chemicon). For example, the neurosphere cells derived from CD133$^+$ CD24$^{-/lo}$ sorted CNS-SC available from StemCells Inc. (Palo Alto, Calif.) express nestin. After expansion, the expanded neurosphere cells were transplanted into neonatal NOD-SCID mice as described. They displayed robust engraftment as equivalent as we observed from neurosphere cells derived from CD133+CD24−/lo CNS-SC. When induced to differentiate, the CD49f$^+$ CD24$^{-/lo}$ sorted/expanded neurosphere cells could differentiate into neurons in morphology, which express b-tubulin III and mature astrocytes morphology which express GFAP. In this particular differentiation assay, neurosphere cells will be cultured onto a poly-ornithine coated surface in the presence of 0-1% FBS, BDNF, GDNF or Epo without EGF, FGF-2 and LIF.

Other differentiation assays can be used to induce differentiation of NS-IC to neurons, astrocytes and oligodendrocytes.

The quantitative NS-IC assay can be performed on unpurified tissue cells, on CD49f$^+$ sorted cells, and on clonal neurosphere cell lines.

EXAMPLE 3

Cell Culture Media for Growth and Passage of NS-IC

Weiss et al., U.S. Pat. No. 5,750,376 and Weiss et al., U.S. Pat. No. 5,851,832 disclose "culture medium containing one or more predetermined growth factors effective for inducing multipotent neural stem cell proliferation" and "differentiation-inducing conditions". However, different basal media can be used, including, but not limited to:

D-MEM/F12 (Gibco BRL, Gaithersburg, Md.);

X vivo 15 (Bio Whittaker, Walkersville, Md.);

Neural progenitor basal media, (Clonetics. San Diego, Calif.); or combinations of the basal media listed above.

A typical media formulation to culture human neurosphere cells is provided in TABLE 1.

TABLE 1

Serum-Free N2/EGF Supplemented Culture Medium For Neurospheres

| Quantity | Reagents |
|---|---|
| 87 ml | DMEM/F12 (Gibco lot. 1012915; Cat. No. 11330-032) |
| 1 ml | N-2 Supplement (Gibco lot 1017018; Cat. No. 17502-014) |
| 1 ml | 0.2 mg/ml heparin (Sigma lot 28H0320; Cat. No. H-3149) |
| 1 ml | 0.2 M Glutamine (JCR lot 7N2320; Cat. No. 59202-77p) |
| 10 ml | 3% Glucose (Sigma, lot 37H0841; Cat. No. G-7021) |
| 20 µl | 100 µg/ml EGF (R&D lot CE107091; Cat. No. 236-EG) |
| 100 µl | 20 µg/ml FGF-2 (Gibco lot KCQ411; Cat. No. 13256-029) |
| 100 µl | 10 µg/ml LIF (R&D lot OX038021; Cat. No. 250-L) |

EGF is added to 100 ml base medium for human neurospheres after filtering the medium. EGF is relatively stable in the medium. FGF-2 and LIF are added when medium is ready to use. The final concentrations of the supplement reagents are:

| | |
|---|---|
| 5 µg/ml | Insulin |
| 100 µg/ml | Human transferrin |
| 6.3 µg/ml | Progesterone |
| 16.1 µg/ml | Putrascine |
| 5.2 ng/ml | Selenite |
| 20 ng/ml | EGF |
| 20 ng/ml | FGF-2 |
| 10 ng/ml | LIF |
| 2 µg/ml | Heparin |
| 2 mM | L-glutamine |
| 6 mg/ml | Glucose |

The optimization of media formulation permits a higher percentage of neurospheres initiated from primary brain tissue to be established. X vivo 15 media is preferred. The optimization of media formulation also permits a more consistent growth of neurospheres.

EXAMPLE 4

CD49f is a Critical Cell Surface Marker Expressed on Cells from Long-term Neurospher Culture A long-term neurosphere cells culture can be obtained from StemCells, Inc (Palo Alto, Calif.). The majority of cells express CD133 (>90%) and CD49f (>80%). When X Vivo 15 is used as basal media, higher percentage of neurosphere cultures initiated from 18 g.w. It is therefore possible to evaluate CD49f cells increases as neurosphere develops. Once neurosphere cells are well established, virtually all cells forming neurospheres express CD133 and CD49f (FIG. 5).

EXAMPLE 5

Neurosphere-Initiating Cells (NS-IC) can be Separated Based on CD15 Expression: Flow Cytometry Cell Sorting (FACS) Approach to Isolate CD15$^+$ CD24$^{-/lo}$ and CD133$^+$CD15$^{-/lo}$CD24$^{-/lo}$ Fetal Brain Cells The purpose of this EXAMPLE is to test whether CD15$^{hi}$ cells are the only cells in the brain that have pluripotent NSC activity. To measure neural stem cells and primitive progenitor activities, a NS-IC assay is established to determine frequency of NS-IC in a given population. When NS-IC are rare and express CD15 antigen, NS-IC can be enriched by CD15$^+$ selection, and correspondingly depleted in other fractions.

Source of monoclonal antibodies: CD15 antigen is recognized by at least the following monoclonal antibody: MMA (BD Biosciences (www.bdbiosciences.com) (catalog numbers 340703, 340850, 347420, 347423, 559045)).

Human fetal brain (FBR 10-20 gestational week ["g.w"]) were obtained after obtaining informed consent. Human fetal brain tissues are cut into 1-3 mm cubed pieces using scalpels, transferred into 5 mL centrifuge tube and washed once with 0.02% EDTA/PBS solution. Tissue pieces were dissociated enzymatically in the presence of collagenase and hyaluronidase at 37 degrees or 1 hour and stored over night at 4 degrees.

During the next days, the dissociated tissue pieces were washed once with 0.02% EDTA/PBS solution and dissociated enzymatically in the presence of trypsin at 37 degrees for 15 minutes. Debris and aggregates are removed by filtering cell suspensions through 70 micron filter cup. Typically $1-10\times10^8$ cells were obtained from each FBr tissue, 16-20 gestational wk. Cells were resuspended in HBSS buffer containing 0.1% human serum albumin and 10 mM HEPES.

The staining and sorting of CNS-SC from FBr are performed as follows. Typically the dissociated FBr cells are incubated and stained with mAb against CD133, CD15, and CD24. Stained cells are washed and resuspended in HBSS containing 0.1% human serum albumin, 10 mM HEPES (Gibco) and 0.5 µg/mL of propidium iodine (PI) and sorted with a dual-laser Vantage SE (BDIS).

NS-IC activity is highly enriched in the both CD133+ $CD15^{hi}$ CD24-/lo and CD133+CD15-/lo CD24-/lo cell population (FIG. 7). Virtually no NI-IC cells were detected from CD15-/lo CD24 hi cell population $CD15^{hi}CD24^{-/lo}$ FACS separated cells are cultured in X vivo 15 or combination of X vivo 15, D-MEM,/F-12 media is used as a basal media. To maximize neurosphere development, the sorted cells are typically cultured in the presence of LIF, FGF-2, EGF, as described in Example 3. Neurosphere cells established from $CD15^{hi}CD24^{-/lo}$ sorted cells will express nestin, as can be tested after approximately 7 days in culture and can be detected with mouse anti-human nestin antibody (Chemicon). For example, the neurosphere cells available from StemCells Inc. (Palo Alto, Calif.) express nestin. When induced to differentiate, the $CD15^{hi}CD24^{-/lo}$ sorted/expanded neurosphere cells can be differentiated into neurons in morphology which express b-tubulin III and mature astrocytes morphology which express GFAP. In this particular differentiation assay, neurosphere cells will be cultured onto a poly-ornithine coated surface in the presence of 0-1% FBS, BDNF, GDNF or Epo without EGF, FGF-2 and LIF.

Other differentiation assays can be used to induce differentiation of NS-IC into neurons, astrocytes and oligodendrocytes. Upon differentiation, $CD133^+CD15^{-/lo}CD24^{-/lo}$ cells are multipotential (FIG. 6).

EXAMPLE 6

Transpatation of $CD49f^+$ $CD24^{-/lo}$ and $CD133^+$ $CD15^{-/lo}$ $CD24^{-/lo}$ Sorted/Expanded Neurosphere Cells into Neonatal NOD-SCID Mice NOD SCID mice have provided an excellent model system for the engraftment of a number of different human cell types including the hematopoietic stem cell. Expanded $CD49f^+CD24^{-/lo}$ or $CD133^+CD15^{-/lo}CD24^{-/lo}$ neurosphere cells at passages 6-10 are harvested and gently dissociated with collagenase. Neonatal mice (P0-P1) are anesthetized by placing them in ice for 5-10 minutes. Once cryo-anesthetized, the pups are placed on a stereotaxic device and injected with 1-2 ul of cells ranging from $10^5-10^6$ cells/injection into the lateral ventricle. The injected mice are kept 18-27 weeks prior to testing the engraftment of human cells.

Generation of Human Specific Monoclonal Antibodies for Tracking Human Cells in Vivo Human CNS-SC neurospheres were transplanted into the lateral ventricle of NOD-Scid neonatal mice. Newborn (P0-P1) mice were injected with $10^5$ cells/site into each lateral ventricle. Human cell engraftment was assessed 1-10 months after transplantation by immunohistochemistry.

Due to inter-species conservation in the sequence of proteins used to characterize neural cells (>90% homology in many cases), most commercially available monoclonal antibodies (mAbs) against neural cells (e.g. β-tubulin III, GFAP, MBP) recognize their antigens in the mouse, rat, primate and human. Extensive testing of commercially available mAbs failed to identify any that would distinguish human cells in a xenogeneic recipient. Therefore, a panel of human specific mAbs was generated at SCI that has been invaluable for the assessment of engraftment and migration of human cells. Extensive testing on mouse and rat brains confirmed that they do not cross-react with their neural cells. Among the SC121 has been routinely and reproducibly used as a marker of human cell engraftment in NOD-Scid recipients. Western blot analysis indicates that SC121 recognizes a 25 kDA protein found in human cells but absent from mouse cells. Immunohistochemical staining with non-transplanted rat brains show there is no cross reactivity in rat brains as well. StemCells Inc. has generated human specific mAbs that distinguish specific neural lineages such as neurons, astrocytes and oligodendrocytes (Table 3). These human specific reagents have been invaluable for the assessing engraftment, migration and differentiation of human cells. For quantitation of human engraftment, it is possible to perform in situ hybridization using human specific DNA probe for Alu-1 repeats.

TABLE 3 mAb and DNA probe for monitoring hCNS-SC

| Name | Antigen | Source | Specificity |
| --- | --- | --- | --- |
| SC101 | Human nuclei | StemCells Inc. | A subset of human nuclei |
| SC112 | N-CAM | StemCells Inc. | Human neuronal lineage |
| SC121 | Cytoplasmic protein | StemCells Inc. | Pan-human |
| SC123 | Human GFAP | StemCells Inc. | Human GFAP+ cells |
| Alu-1 | DNA probe in situ | StemCells Inc. | All human nuclei |

Six to 36 weeks post-transplantation, the injected mice are perfused with 4% paraformaldehyde. The mouse brains are sectioned sagitally at 40 um thickness. To detect transplanted human cells, sections will be incubated with mab SC121 (StemCells, Inc.), followed by incubation with a biotinylated goat anti-mouse IgG and the components of the VECTASTAIN ELITE ABC kit, using the methods employed in preliminary studies. The antibody-immunoperoxidase complex will be detected using the NovaRED substrate (Vector, Burlingame, Calif.).

To evaluate in vivo engraftment migration and the differentiation capacity of hCNS-SC, $10^5$ cells from $CD49f^{30}$ $CD24^{-/lo}$ or $CD133^+$ $CD15^+CD24^{-/lo}$ sorted/expanded neurosphere cultures at passage 7-10 can be injected into the lateral ventricles of neonatal NOD-SCID mice. Similar to $CD133^+$ CD24-/lo sorted/expanded neurosphere cells, they engrafted robustly, migrate into olfactory bulb and hippocampus, and differentiate into neuron and glia morphologically (FIG. 7).

REFERENCES

Allendoerfer, K. L., Magnani, J. L., and Patterson, P. H. (1995). FORSE-1, an antibody that labels regionally restricted subpopulations of progenitor cells in the embryonic central nervous system, recognizes the $Le^x$ carbohydrate on a proteoglycan and two glycolipid antigens. Mol. Cell. Neurosci. 6, 381-395.

Allendoerfer, K. L., Durairaj, A., Matthews, G. A., and Patterson, P. H. (1999). Morphological domains of Lewis- X/FORSE-1 immunolabeling in the embryonic neural tube are due to developmental regulation of cell surface carbohydrate expression. Dev. Biol. 211, 208-219.

Ashwell, K. W. S., and Mai, J. K. (1997). Developmental expression of the CD15 epitope in the hippocampus of the mouse. Cell Tissue Res. 289, 17-23.

Bach, S. P., Renehan, A. G., and Potten, C. S. (2000). Stem cells: the intestinal stem cell as a paradigm. Carcinogenesis 21, 469-476.

Bartsch, D., and Mai, J. K. (1991). Distribution of the 3-fucosyl-N-acetyl-lactosamine (FAL) epitope in the adult mouse brain. Cell Tissue Res. 263, 353-366.

Bird, J. M., and Kimber, S. J. (1984). Oligosaccharides containing fucose linked alpha (1-3) and alpha (1-4) to N-acetylglucosamine cause decompaction of mouse morulae. Dev. Biol. 104, 449-460.

Cao, Q. L., Zhang, Y. P., Howard, R. M., Walters, W. M., Tsoulfas. P., and Whittemore, S. R. (2001). Pluripotent stem cells engrafted into the normal or lesioned adult rat spinal cord are restricted to a glial lineage. Exp. Neurol. 167, 48-58.

Calaora, V., Chazal, G., Nielsen, P. J., Rougon, G., and Moreau, H. (1996). mCD24 expression in the developing mouse brain and in zones of secondary neurogenesis in the adult. Neuroscience 73, 581-594.

Campos-Ortega, J. A. (1995). Genetic mechanisms of early neurogenesis in Drosophila melanogaster. Mol. Neurobiol. 10, 75-89.

Chiasson, B. J., Tropepe, V., Morshead, C. M., and Van der Kooy, D. (1999). Adult mammalian forebrain ependymal and subependymal cells demonstrate proliferative potential, but only subependymal cells have neural stem cell characteristics. J. Neurosci. 19, 4462-4471.

Davis, A. A. and Temple, S. (1994) A self-renewing multipotential stem cell in embryonic rat cerebral cortex. Nature 372, 263-266.

Dodd, J., and Jessell, T. M. (1986). Cell surface glycoconjugates and carbohydrate-binding proteins: possible recognition signals in sensory neurone development. J. Exp. Biol. 129, 225-238.

Doetsch, F., Caille, I., Lim, D. A., Garcia-Verdugo, J. M., and Alvarez-Buylla, A. (1999a). Subventricular zone astrocytes are neural stem cells in the adult mammalian brain. Cell 97, 703-716.

Doetsch, F., Garcia-Verdugo, J. M., and Alvarez-Buylla, A. (1999b). Regeneration of a germinal layer in the adult mammalian brain. Proc. Natl. Acad. Sci. USA 96, 11619-11624.

Dvorak, P., Hampl, A., Jirmanova, L., Pacholikova, J., and Kusakabe, M., (1998). Embryoglycan ectodomains regulate biological activity of FGF-2 to embryonic stem cells. J. Cell Science 111, 2945-2952.

Fox, N., Damjanov, I., Martinez-Hernandez A., Knowles, B. B., and Solter, D. (1981). Immunohistochemical localization of the early embryonic antigen in postimplantation mouse embryos and fetal and adult tissues. Dev. Biol. 83, 391-398.

Gage, F. H. (2000). Mammalian neural stem cells. Science 287, 1433-1438.

Gooi, H. C., Feizi, T., Kapadia, A., Knowles, B. B., Solter, D., and Evans, M. J. (1981). Stage-specific embryonic antigen involves alpha 1 goes to 3 fucosylated type 2 blood group chains. Nature 292, 156-158.

Gomperts, M., Garcia-Castro, M., Wylie, C, and Heasman, J. (1994). Interactions between primordial germ cells play a role in the migration in mouse embryos. Development 120, 135-141.

Gocht, A., Struckhoff, G., and Löhler, J. (1996). CD15-containing glycoconjugates in the central nervous system. Histol. Histopathol. 11, 1007-1028.

Gould, E., Reeves, A. J., Graziano, M. S., and Gross, C. G. (1999). Neurogenesis in the neocortex of adult primates. Science 286, 548-552.

Gritti, A., Parati., E. A., Cova, L., Frolichsthal, P., Galli, R., Wanke, E., Faravelli, L., Morassutti, D. J., Roisen, F., Nickel, D. D., and Vescovi, A. L. (1996). Multipotential stem cells from the adult mouse brain proliferate and self-renew in response to basic fibroblast growth factor. J. Neurosci. 16, 1091-1100.

Gritti, A., Bonfanti L., Doetsch, F., Caille I., Alvarez-Buylla, A., Lim, D. A., Galli, R., Verduga, J. M., Herrara, D. G., Vescovi, A. L. (2002). Multipotent neural stem cells reside into the rostral extension and olfactory bulb of adult rodents. J Neurosci. 22,437-45.

Hakomori, S. I. (1992). LewisX and related structures as adhesion molecules. Histochem. J. 24, 771-776.

Jessell, T. M., Hynes, M. A., and Dodd, J. (1990). Carbohydrates and carbohydrate-binding proteins in the nervous system. Ann. Rev. Neurosci. 13, 227-255.

Jirmanova, L., Pacholikova, J., Krejci, P., Hampl, A., and Dvorak, P. (1999). O-linked carbohydrates are required for FGF-2-mediated proliferation of mouse embryonic cells. Int. J. Dev. Biol. 43, 555-562.

Johansson, C. B., Momma, S., Clarke, D. L., Risling, M., Lendahl, U., and Frisen, J. (1999). Identification of a neural stem cell in the adult mammalian central nervous system. Cell 96, 25-34.

Jones, P. H., Harper, S., and Watt, F. M. (1995). Stem cell patterning and fate in human epidermis. Cell 80, 83-93.

Kato, M., Wang, H., Kainulainen, V., Fitzgerald, M. L., Ledbetter, S., Ornitz, D. M., and Bernfield, M. (1998). Physiological degradation converts the soluble syndecan-1 ectodomain from an inhibitor to a potent activator of FGF2. Nat. Med. 4, 691-697.

Kawaguchi, A., Miyata, T., Sawamoto, K., Takashita, N., Murayama, A., Akamatsu, W., Ogawa, M., Okabe, M., Tano, Y., Goldman, S. A., and Okano, H. (2001). Nestin-EGFP transgenic mice: visualization of the self-renewal and multipotency of CNS stem cells. Mol. Cell. Neurosci. 17, 259-273.

Kempermann, G., Kuhn, H. G., and Gage, F. H. (1997). Genetic influence on neurogenesis in the dentate gyrus of adult mice. Proc. Natl. Acad. Sci. USA 94, 10409-10414.

Kondo, T., and Raff, M. (2000). Oligodendrocyte precursor cells reprogrammed to become multipotential CNS stem cells. Science 289, 1754-1757.

Laywell, E. D., Rakic, P., Kukekov, V. G., Holland, E. C., and Steindler, D. A. (2000). Identification of a multipotent astrocytic stem cell in the immature and adult mouse brain. Proc. Natl. Acad. Sci. USA 97, 13883-13888.

Lois, C., and Alvarez-Buylla, A. (1993). Proliferating subventricular zone cells in the adult mammalian forebrain can differentiate into neurons and glia. Proc. Natl. Acad. Sci. USA 90, 2074-2077.

Mai, J. K., Andressen, C., and Ashwell, K. W. (1998). Demarcation of prosencephalic regions by CD15-positive radial glia. Eur. J. Neurosci.10, 746-751.

Marani, E. and Tetteroo, P. A. (1983). A longitudinal band-pattem for the monoclonal human granulocyte antibody B4,3 in the cerebellar external granular layer of the immature rabbit. Histochemistry 78, 157-161.

Marani, E., van Oers, J. W., Tetteroo, P. A., Poelmann, R. E., van der Veeken J., and Deenen, M. G. (1986). Stage specific embryonic carbohydrate surface antigens of primordial germ cells in mouse embryos: FAL (SSEA-1) and globoside (SSEA-3). Acta. Morphol. Neerl. Scand. 24, 103-110.

Marmur, R., Mabie, P. C., Gokhan, S., Song, Q., Kessler, J. A., and Mehler, M. F. (1998). Isolation and developmental characterization of cerebral cortical multipotent progenitors. Dev. Biol. 204, 577-591.

Milev, P., Monnerie, H., Popp, S., Margolis, R. K., and Margolis, R. U. (1998). The core protein of the chondroitin sulfate proteoglycan phosphacan is a high-affinity ligand of fibroblast growth factor-2 and potentiates its mitogenic activity. J. Biol. Chem. 273, 21439-21442.

Morrison S. J., Shah, N. M. and Anderson, D. J. (1997). Regulatory mechanisms in stem cell biology. Cell 88, 287-298.

Morrison, S. J., White, P. M., Zock, C., and Anderson, D. J. (1999). Prospective identification, isolation by flow cytometry, and in vivo self-renewal of multipotent mammalian neural crest cells. Cell 96, 737-749.

Morshead, C. M., Reynolds, B. A., Craig, C. G., McBurney, M. W., Staines, W. A., Morassutti, D., Weiss, S., and Van der Kooy, D. (1994). Neural stem cells in the adult mammalian forebrain: a relatively quiescent subpopulation of subependymal cells. Neuron 13, 1071-1082.

Muramatsu, T. (1994). Cell surface glycoproteins: biochemical, immunological and molecular biological studies. Nagoya J. Med. Sci. 57, 95-108.

Nowakowski, R. S. and Hayes, N. L. (2000). New neurons: extraordinary evidence or extraordinary conclusion? Science 288, 771-772.

Palmer, T. D., Takahashi, J., and Gage, F. H. (1997). The adult rat hippocampus contains primordial neural stem cells. Mol. Cell. Neurosci. 8, 389-404.

Palmer, T. D., Willhoite, A. R., and Gage, F. H. (2000). Vascular niche for adult hippocampal neurogenesis. J. Comp. Neurol. 425, 479-494.

Rietze, R., Valcanis, H., and Bartlett, P. (2001). Purification of a pluripotent neural stem cells from the adult brain. Nature 412, 736-739.

Reynolds, R. and Hardy, R. (1997). Oligodendroglial progenitors labeled with the O4 antibody persist in the adult rat cerebral cortex in vivo. J. Neurosci. Res. 47, 455-470.

Reynolds, B. A., and Weiss, S. (1992). Generation of neurons and astrocytes from isolated cells of the adult mammalian central nervous system. Science 255, 1707-1710.

Sakakibara, S., Imai, T., Hamaguchi, K., Okabe, M., Aruga, J., Kakajima, Y., Yasutomi, D., Nagata, T., Kurihara, Y., Uesugi, S., Miyata, T., Ogawa, M., Mikoshiba, K. and Okano, H. (1996). Mouse-Musashi-1, a neural RNA-binding protein highly enriched in the mammalian CNS stem cell. Dev. Biol. 176, 230-242.

Seaberg, R. M., and van der Kooy, D. (2002). Adult rodent neurogenic regions: the ventricular subependyma contains neural stem cells, but the dentate gyrus contains restricted progenitors. J. Neurosci. 22, 1784-93.

Solter, D., and Knowles, B. B. (1978). Monoclonal antibody defining a stage-specific mouse embryonic antigen (SSEA-1). Proc. Natl. Acad. Sci. USA 75, 5565-5569.

Suhonen, J. O., Peterson, D. A., Ray, J., and Gage, F. H. (1996). Differentiation of adult hippocampus-derived progenitors into olfactory neurons in vivo. Nature 383, 624-627.

Tole, S., Kaprielian, Z., Ou, S. K., and Patterson, P. H. (1995). FORSE-1: a positionally regulated epitope in the developing rat central nervous system. J. Neurosci. 15, 957-969.

Uchida, N., Buck, D. W., He, D., Reitsma, M. J., Masek, M., Phan, T. V., Tsukamoto, A. S., Gage, F. H., and Weissman, I. L. (2000). Direct isolation of human central nervous system stem cells. Proc. Natl. Acad. Sci. USA 97, 14720-14725.

Weiss, S., Dunne, C., Hewson, J., Wohl, C., Wheatley, M., Peterson, A. C., and Reynolds, B. (1996). Multipotent stem cells are present in the adult mammalian spinal cord and ventricular neuroaxis. J. Neurosci. 16, 7599-7609.

Winkler, C., Fricker, R. A., Gates, M. A., Olsson, M., Hammang, J. P., Carpenter, M. K., and Bjorklund, A. (1998). Incorporation and glial differentiation of mouse EGF-responsive neural progenitor cells after transplantation into the embryonic rat brain. Mol Cell Neurosci. 11, 99-116.

Yamamoto, M., Boyer, A. M., and Schwarting, G. A. (1985). Fucose-containing glycolipids are stage- and region-specific antigens in developing embryonic brain of rodents. Proc. Natl. Acad. Sci. USA 82, 3045-3049.

OTHER EMBODIMENTS

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A method of producing a population from neural tissue enriched for human central nervous system stem cells (CNS-SC) which can initiate neurospheres (NS-IC), comprising:
   a) contacting neural or neural derived cells with a monoclonal antibody that binds to CD49f; and
   b) selecting said neural or neural-derived cells that bind to the monoclonal antibody; wherein the selected cells are enriched for human CNS-SC.

2. The method of claim 1, wherein the monoclonal antibody is fluorochrome conjugated.

3. The method of claim 1, wherein the monoclonal antibody is conjugated to magnetic particles.

4. The method of claim 1, wherein the selecting is by flow cytometry, fluorescence activated cell sorting, or high gradient magnetic selection.

5. The method of claim 1, wherein the population containing neural or neural-derived cells is obtained from a neurosphere culture or an adherent culture.

6. The method of claim 1, wherein the population containing neural or neural-derived cells is obtained from primary neural tissue.

7. The method of claim 1, further comprising the steps of further enriching a population from neural tissue for CNS-SC by
   c) contacting the selected cells with a second monoclonal antibody that binds to the CD24 antigen; and
   d) removing those cells that bind to the second monoclonal antibody, wherein the selected cells in the population are $CD24^{-/lo}$ and are enriched for CNS-SC.

8. The method of claim 7, wherein the second monoclonal antibody is monoclonal antibody SC20.

9. The method of claim 1, further comprising the steps of further enriching a population for CNS-SC by
   c) contacting the selected cells with a monoclonal antibody that binds to CD133; and
   d) further selecting those cells that bind to the monoclonal antibody that binds to CD133,
   wherein the further selected cells are enriched for CNS-SC.

10. The method of claim 1, wherein the neural or neural derived cells are contacted with a monoclonal antibody that binds to CD133 prior to the contacting of step a).

11. The method of claim 9 or 10, wherein the monoclonal antibody that binds to CD133 is monoclonal antibody AC133.

12. A method for producing a population enriched for human central nervous system stem cells (CNS-SC), which can initiate neurospheres (NS-IC) or an adherent cell culture comprising selecting from a population of neural or neural-derived cells for those cells that are $CD49f^+$, wherein said population is enriched by selecting for cells that bind to an anti-CD49f antibody selected from the group consisting of monoclonal antibody GoH3 and monoclonal antibody 4F10 and removing those cells that do not bind to the anti-CD49f antibody.

13. The method of claim 12, further comprising the step of further enriching the population obtained from primary neural tissues for CNS-SC by selecting the cells that are $CD24^{-/lo}$ from the remaining population of neural or neural-derived cells.

14. The method of claim 13, further comprising the step of further enriching the population by removing the cells that bind to monoclonal antibody SC20, which recognizes CD24.

15. A method for enriching from a population of neural cells for the populations of neurosphere initiating stem cell (NS-IC) fraction, comprising selecting from the neural cells for cells that express CD49f by binding to monoclonal antibody GoH3 or monoclonal antibody 4F10, wherein the selected cells are enriched in the fraction of NS-IC as compared with the population of neural cells.

16. The method of claim 15, further comprising the step of further enriching for the fraction of NS-IC from primary tissues by removing the cells that are $CD24^+$, wherein the remaining cells are $CD24^{-/lo}$.

17. A method for isolating a neurosphere initiating stem cell (NS-IC) from primary neural tissues, comprising:
   a) selecting from a population of neural or neural-derived cells for cells that are $CD49f^+$;
   b) removing the cells that are $CD24^+$, wherein the remaining cells are $CD24^{-/lo}$;
   c) introducing the cells remaining after step b) to a serum-free culture medium containing one or more growth factors selected from the group consisting of leukemia inhibitory factor (LIF), epidermal growth factor (EGF), basic fibroblast growth factor (bFGF; FGF-2), and combinations thereof; and
   d) proliferating the remaining cells in the culture medium.

18. A method for producing a population enriched for human central nervous system stem cells (CNS-SC) which can initiate neurospheres (NS-IC) comprising selecting from neural or neural-derived cells for cells that are $CD49f^+$ and bind to an anti-CD49f antibody selected from the group consisting of monoclonal antibody GoH3 and monoclonal antibody 4F10, to produce a population enriched for CNS-SC, wherein the selecting is by attachment to and disattachment from solid phase.

19. A method for the enrichment of human central nervous system neural stem cells (CNS-SC), which can initiate neurospheres (NS-IC); progenitors; or a combination thereof, said method comprising:
   a) combining a population of neural or neural-derived cells with a reagent that binds to the CD49f antigen, wherein the reagent is at least one antibody selected from the group consisting of monoclonal antibody GoH3 and monoclonal antibody 4F10; and
   b) selecting for those cells that bind to the reagent, wherein the selected cells are enriched for CNS-SC, progenitors, or a combination thereof.

20. A method for producing a population enriched for human central nervous system stem cells (CNS-SC), which can initiate neurospheres (NS-IC); progenitors; or a combination thereof, comprising selecting from neural or neural-derived cells for those cells that express CD49f and bind to monoclonal antibody GoH3 or to monoclonal antibody 4F10, to produce a population enriched for CNS-SC, progenitors, or a combination thereof.

21. The method of claim 20, wherein the antibody is monoclonal antibody GoH3.

22. The method of claim 20, wherein the antibody is monoclonal antibody 4F10.

23. The method of claim 20, wherein the population containing neural or neural-derived cells is obtained from a neurosphere culture or an adherent monolayer culture.

24. The method of claim 20, wherein the population containing neural or neural-derived cells is obtained from neural tissue.

25. A method for producing a population enriched for human central nervous system stem cells (CNS-SC), which can initiate neurospheres (NS-IC); progenitors; or a combination thereof, wherein the population is obtained from primary neural tissues, the method comprising selecting from a population of neural or neural-derived cells for cells that are CD49f⁺ and that bind to an anti-CD49f antibody selected from the group consisting of monoclonal antibody GoH3 and monoclonal antibody 4F10, the method further comprising the steps of further enriching for CNS-SC, progenitors, or a combination thereof, by further selecting for those cells that are CD24$^{-/lo}$.

26. A method for isolating a neurosphere initiating stem cell (NS-IC), comprising:
   a) selecting from a population of neural or neural-derived cells for at least one selected cell that binds to monoclonal antibody GoH3 or to monoclonal antibody 4F10;
   b) introducing at least one selected cell to a serum free culture medium containing one or more growth factors selected from the group consisting of leukemia inhibitory factor (LIF), epidermal growth factor (EGF), basic fibroblast growth factor (FGF-2) and combinations thereof; and
   c) proliferating the at least one selected cell in the culture medium.

* * * * *

SEQUENCE LISTING

```
<160> NUMBER OF SEQ ID NOS: 2

<210> SEQ ID NO 1
<211> LENGTH: 1130
<212> TYPE: PRT
<213> ORGANISM: Homo sapiens

<400> SEQUENCE: 1

Met Ala Ala Ala Gly Gln Leu Cys Leu Leu Tyr Leu Ser Ala Gly Leu
1               5                   10                  15

Leu Ser Arg Leu Gly Ala Ala Phe Asn Leu Asp Thr Arg Glu Asp Asn
                20                  25                  30
```

-continued

```
Val Ile Arg Lys Tyr Gly Asp Pro Gly Ser Leu Phe Gly Phe Ser Leu
            35                  40                  45

Ala Met His Trp Gln Leu Gln Pro Glu Asp Lys Arg Leu Leu Leu Val
 50                  55                  60

Gly Ala Pro Arg Gly Glu Ala Leu Pro Leu Gln Arg Ala Asn Arg Thr
 65                  70                  75                  80

Gly Gly Leu Tyr Ser Cys Asp Ile Thr Ala Arg Gly Pro Cys Thr Arg
                 85                  90                  95

Ile Glu Phe Asp Asn Asp Ala Asp Pro Thr Ser Glu Ser Lys Glu Asp
                100                 105                 110

Gln Trp Met Gly Val Thr Val Gln Ser Gln Gly Pro Gly Gly Lys Val
            115                 120                 125

Val Thr Cys Ala His Arg Tyr Glu Lys Arg Gln His Val Asn Thr Lys
        130                 135                 140

Gln Glu Ser Arg Asp Ile Phe Gly Arg Cys Tyr Val Leu Ser Gln Asn
145                 150                 155                 160

Leu Arg Ile Glu Asp Asp Met Asp Gly Gly Asp Trp Ser Phe Cys Asp
                165                 170                 175

Gly Arg Leu Arg Gly His Glu Lys Phe Gly Ser Cys Gln Gln Gly Val
            180                 185                 190

Ala Ala Thr Phe Thr Lys Asp Phe His Tyr Ile Val Phe Gly Ala Pro
        195                 200                 205

Gly Thr Tyr Asn Trp Lys Gly Ile Val Arg Val Glu Gln Lys Asn Asn
    210                 215                 220

Thr Phe Phe Asp Met Asn Ile Phe Glu Asp Gly Pro Tyr Glu Val Gly
225                 230                 235                 240

Gly Glu Thr Glu His Asp Glu Ser Leu Val Pro Val Pro Ala Asn Ser
                245                 250                 255

Tyr Leu Gly Leu Leu Phe Leu Thr Ser Val Ser Tyr Thr Asp Pro Asp
            260                 265                 270

Gln Phe Val Tyr Lys Thr Arg Pro Arg Glu Gln Pro Asp Thr Phe
        275                 280                 285

Pro Asp Val Met Met Asn Ser Tyr Leu Gly Phe Ser Leu Asp Ser Gly
    290                 295                 300

Lys Gly Ile Val Ser Lys Asp Glu Ile Thr Phe Val Ser Gly Ala Pro
305                 310                 315                 320

Arg Ala Asn His Ser Gly Ala Val Val Leu Leu Lys Arg Asp Met Lys
                325                 330                 335

Ser Ala His Leu Leu Pro Glu His Ile Phe Asp Gly Glu Gly Leu Ala
            340                 345                 350

Ser Ser Phe Gly Tyr Asp Val Ala Val Val Asp Leu Asn Lys Asp Gly
        355                 360                 365

Trp Gln Asp Ile Val Ile Gly Ala Pro Gln Tyr Phe Asp Arg Asp Gly
    370                 375                 380

Glu Val Gly Gly Ala Val Tyr Val Tyr Met Asn Gln Gln Gly Arg Trp
385                 390                 395                 400

Asn Asn Val Lys Pro Ile Arg Leu Asn Gly Thr Lys Asp Ser Met Phe
                405                 410                 415

Gly Ile Ala Val Lys Asn Ile Gly Asp Ile Asn Gln Asp Gly Tyr Pro
            420                 425                 430

Asp Ile Ala Val Gly Ala Pro Tyr Asp Asp Leu Gly Lys Val Phe Ile
        435                 440                 445

Tyr His Gly Ser Ala Asn Gly Ile Asn Thr Lys Pro Thr Gln Val Leu
```

-continued

```
            450                 455                 460
Lys Gly Ile Ser Pro Tyr Phe Gly Tyr Ser Ile Ala Gly Asn Met Asp
465                 470                 475                 480

Leu Asp Arg Asn Ser Tyr Pro Asp Val Ala Val Gly Ser Leu Ser Asp
                485                 490                 495

Ser Val Thr Ile Phe Arg Ser Arg Pro Val Ile Asn Ile Gln Lys Thr
                500                 505                 510

Ile Thr Val Thr Pro Asn Arg Ile Asp Leu Arg Gln Lys Thr Ala Cys
                515                 520                 525

Gly Ala Pro Ser Gly Ile Cys Leu Gln Val Lys Ser Cys Phe Glu Tyr
530                 535                 540

Thr Ala Asn Pro Ala Gly Tyr Asn Pro Ser Ile Ser Ile Val Gly Thr
545                 550                 555                 560

Leu Glu Ala Glu Lys Glu Arg Arg Lys Ser Gly Leu Ser Ser Arg Val
                565                 570                 575

Gln Phe Arg Asn Gln Gly Ser Glu Pro Lys Tyr Thr Gln Glu Leu Thr
                580                 585                 590

Leu Lys Arg Gln Lys Gln Lys Val Cys Met Glu Glu Thr Leu Trp Leu
                595                 600                 605

Gln Asp Asn Ile Arg Asp Lys Leu Arg Pro Ile Pro Ile Thr Ala Ser
                610                 615                 620

Val Glu Ile Gln Glu Pro Ser Ser Arg Arg Val Asn Ser Leu Pro
625                 630                 635                 640

Glu Val Leu Pro Ile Leu Asn Ser Asp Glu Pro Lys Thr Ala His Ile
                645                 650                 655

Asp Val His Phe Leu Lys Glu Gly Cys Gly Asp Asp Asn Val Cys Asn
                660                 665                 670

Ser Asn Leu Lys Leu Glu Tyr Lys Phe Cys Thr Arg Glu Gly Asn Gln
                675                 680                 685

Asp Lys Phe Ser Tyr Leu Pro Ile Gln Lys Gly Val Pro Glu Leu Val
                690                 695                 700

Leu Lys Asp Gln Lys Asp Ile Ala Leu Glu Ile Thr Val Thr Asn Ser
705                 710                 715                 720

Pro Ser Asn Pro Arg Asn Pro Thr Lys Asp Gly Asp Ala His Glu
                725                 730                 735

Ala Lys Leu Ile Ala Thr Phe Pro Asp Thr Leu Thr Tyr Ser Ala Tyr
                740                 745                 750

Arg Glu Leu Arg Ala Phe Pro Glu Lys Gln Leu Ser Cys Val Ala Asn
                755                 760                 765

Gln Asn Gly Ser Gln Ala Asp Cys Glu Leu Gly Asn Pro Phe Lys Arg
                770                 775                 780

Asn Ser Asn Val Thr Phe Tyr Leu Val Leu Ser Thr Thr Glu Val Thr
785                 790                 795                 800

Phe Asp Thr Pro Asp Leu Asp Ile Asn Leu Lys Leu Glu Thr Thr Ser
                805                 810                 815

Asn Gln Asp Asn Leu Ala Pro Ile Thr Ala Lys Ala Lys Val Val Ile
                820                 825                 830

Glu Leu Leu Leu Ser Val Ser Gly Val Ala Lys Pro Ser Gln Val Tyr
                835                 840                 845

Phe Gly Gly Thr Val Val Gly Glu Gln Ala Met Lys Ser Glu Asp Glu
                850                 855                 860

Val Gly Ser Leu Ile Glu Tyr Glu Phe Arg Val Ile Asn Leu Gly Lys
865                 870                 875                 880
```

-continued

```
Pro Leu Thr Asn Leu Gly Thr Ala Thr Leu Asn Ile Gln Trp Pro Lys
            885                 890                 895

Glu Ile Ser Asn Gly Lys Trp Leu Leu Tyr Leu Val Lys Val Glu Ser
        900                 905                 910

Lys Gly Leu Glu Lys Val Thr Cys Glu Pro Gln Lys Glu Ile Asn Ser
        915                 920                 925

Leu Asn Leu Thr Glu Ser His Asn Ser Arg Lys Arg Glu Ile Thr
        930                 935                 940

Glu Lys Gln Ile Asp Asp Asn Arg Lys Phe Ser Leu Phe Ala Glu Arg
945                 950                 955                 960

Lys Tyr Gln Thr Leu Asn Cys Ser Val Asn Val Asn Cys Val Asn Ile
                965                 970                 975

Arg Cys Pro Leu Arg Gly Leu Asp Ser Lys Ala Ser Leu Ile Leu Arg
            980                 985                 990

Ser Arg Leu Trp Asn Ser Thr Phe Leu Glu Glu Tyr Ser Lys Leu Asn
            995                 1000                1005

Tyr Leu Asp Ile Leu Met Arg Ala Phe Ile Asp Val Thr Ala Ala
        1010                1015                1020

Ala Glu Asn Ile Arg Leu Pro Asn Ala Gly Thr Gln Val Arg Val
        1025                1030                1035

Thr Val Phe Pro Ser Lys Thr Val Ala Gln Tyr Ser Gly Val Pro
        1040                1045                1050

Trp Trp Ile Ile Leu Val Ala Ile Leu Ala Gly Ile Leu Met Leu
        1055                1060                1065

Ala Leu Leu Val Phe Ile Leu Trp Lys Cys Gly Phe Phe Lys Arg
        1070                1075                1080

Ser Arg Tyr Asp Asp Ser Val Pro Arg Tyr His Ala Val Arg Ile
        1085                1090                1095

Arg Lys Glu Glu Arg Glu Ile Lys Asp Glu Lys Tyr Ile Asp Asn
        1100                1105                1110

Leu Glu Lys Lys Gln Trp Ile Thr Lys Trp Asn Arg Asn Glu Ser
        1115                1120                1125

Tyr Ser
    1130

<210> SEQ ID NO 2
<211> LENGTH: 2861
<212> TYPE: DNA
<213> ORGANISM: Homo sapiens

<400> SEQUENCE: 2
ctgctcctgc gcggcagctg ctttagaagg tctcgagcct cctgtacctt cccagggatg      60
aaccgggcct tccctctgga aggcgagggt tcgggccaca gtgagcgagg gccagggcgg     120
tgggcgcgcg cagagggaaa ccggatcagt tgagagagaa tcaagagtag cggatgaggc     180
gcttgtgggg cgcggcccgg aagccctcgg gcgcgggctg ggagaaggag tgggcggagg     240
cgccgcagga ggctcccggg gcctggtcgg gccggctggg ccccgggcgc agtggaagaa     300
agggacgggc ggtgcccggt tgggcgtcct ggccagctca ccttgccctg gcggctcgcc     360
ccgcccggca cttgggagga gcagggcagg gcccgcggcc tttgcattct gggaccgccc     420
ccttccattc ccgggccagc ggcgagcggc agcgacggct ggagccgcag ctacagcatg     480
agagccggtg ccgctcctcc acgcctgcgg acgcgtggcg agcggaggca gcgctgcctg     540
ttcgcgccat gggggcaccg tggggctcgc cgacggcggc ggcgggcggg cggcgcgggt     600
```

-continued

```
ggcgccgagg ccgggggctg ccatggaccg tctgtgtgct ggcggccgcc ggcttgacgt    660
gtacggcgct gatcacctac gcttgctggg ggcagctgcc gccgctgccc tgggcgtcgc    720
caaccccgtc gcgaccggtg ggcgtgctgc tgtggtggga gcccttcggg gggcgcgata    780
gcgccccgag gccgccccct gactgccggc tgcgcttcaa catcagcggc tgccgcctgc    840
tcaccgaccg cgcgtcctac ggagaggctc aggccgtgct tttccaccac cgcgacctcg    900
tgaaggggcc ccccgactgg ccccgccct ggggcatcca ggcgcacact gccgaggagg    960
tggatctgcg cgtgttggac tacgaggagg cagcggcggc ggcagaagcc ctggcgacct    1020
ccagccccag gccccgggc cagcgctggg tttggatgaa cttcgagtcg ccctcgcact    1080 ccccgggct gcgaagcctg gcaagtaacc tcttcaactg gacgctctcc taccgggcgg    1140
actcggacgt ctttgtgcct tatggctacc tctaccccag aagccacccc ggcgacccgc    1200
cctcaggcct ggccccgcca ctgtccagga acaggggct ggtggcatgg gtggtgagcc    1260
actgggacga gcgccaggcc cgggtccgct actaccacca actgagccaa catgtgaccg    1320
tggacgtgtt cggccggggc gggccgggc agccggtgcc cgaaattggg ctcctgcaca    1380
cagtggcccg ctacaagttc tacctggctt tcgagaactc gcagcacctg gattatatca    1440
ccgagaagct ctggcgcaac gcgttgctcg ctggggcggt gccggtggtg ctgggcccag    1500
accgtgccaa ctacgagcgc tttgtgcccc gcggcgcctt catccacgtg gacgacttcc    1560
caagtgcctc ctccctggcc tcgtacctgc ttttcctcga ccgcaaccc gcggtctatc    1620 gccgctactt ccactggcgc cggagctacg ctgtccacat cacctccttc tgggacgagc    1680
cttggtgccg ggtgtgccag gctgtacaga gggctgggga ccggcccaag agcatacgga    1740
acttggccag ctggttcgag cggtgaagcc gcgctcccct ggaagcgacc caggggaggc    1800
caagttgtca gcttttgat cctctactgt gcatctcctt gactgccgca tcatgggagt    1860
aagttcttca aacacccatt tttgctctat gggaaaaaaa cgatttacca attaatatta    1920
ctcagcacag agatgggggc ccggtttcca tattttttgc acagctagca attgggctcc    1980
ctttgctgct gatgggcatc attgtttagg ggtgaaggag ggggttcttc ctcaccttgt    2040
aaccagtgca gaaatgaaat agcttagcgg caagaagccg ttgaggcggt ttcctgaatt    2100
tccccatctg ccacaggcca tatttgtggc ccgtgcagct tccaaatctc atacacaact    2160
gttcccgatt cacgttttc tggaccaagg tgaagcaaat ttgtggttgt agaaggagcc    2220
ttgttggtgg agagtggaag gactgtggct gcagtggga cttttgttgtt tggattcctc    2280 acagccttgg ctcctgagaa aggtgaggag ggcagtccaa gaggggccgc tgacttcttt    2340
cacaagtact atctgttccc ctgtcctgtg aatggaagca aagtgctgga ttgtccttgg    2400
aggaaactta agatgaatac atgcgtgtac ctcactttac ataagaaatg tattcctgaa    2460
aagctgcatt taaatcaagt cccaaattca ttgacttagg ggagttcagt atttaatgaa    2520
accctatgga gaatttatcc ctttacaatg tgaatagtca tctcctaatt tgtttcttct    2580
gtctttatgt ttttctataa cctggatttt ttaaatcata ttaaaattac agatgtgaaa    2640
ataaagcaga agcaaccttt ttccctcttc ccagaaaacc agtctgtgtt tacagacaga    2700
agagaaggaa gccatagtgt cacttccaca caattattta tttcatgtct ttactggacc    2760
tgaaatttaa actgcaatgc cagtcctgca ggagtgctgg cattaccctc tgcagaacag    2820
tgaaaggtat tgcactacat tatggaatca tgcaaaaaaa a    2861
```